(12) United States Patent
Cravatt et al.

(10) Patent No.: US 8,940,497 B2
(45) Date of Patent: Jan. 27, 2015

(54) ENZYME REGULATING ETHER LIPID SIGNALING PATHWAYS

(75) Inventors: Benjamin F. Cravatt, La Jolla, CA (US); Kyle P. Chiang, Cardiff, CA (US); Sherry Niessen, San Diego, CA (US); Alan Saghatelian, Cambridge, MA (US)

(73) Assignee: The Scripps Research Institute, La Jolla, CA (US)

( * ) Notice: Subject to any disclaimer, the term of this patent is extended or adjusted under 35 U.S.C. 154(b) by 233 days.

(21) Appl. No.: 13/585,298

(22) Filed: Aug. 14, 2012

(65) Prior Publication Data
US 2013/0164758 A1 Jun. 27, 2013

Related U.S. Application Data

(62) Division of application No. 11/866,349, filed on Oct. 2, 2007, now abandoned.

(60) Provisional application No. 60/849,351, filed on Oct. 2, 2006.

(51) Int. Cl.
*A61K 31/325* (2006.01)
*C12Q 1/34* (2006.01)
*G01N 25/02* (2006.01)
*G01N 33/92* (2006.01)

(52) U.S. Cl.
CPC .............. *A61K 31/325* (2013.01); *G01N 33/92* (2013.01); *C12Q 1/34* (2013.01); *G01N 2500/02* (2013.01)
USPC .......... 435/18; 435/6.13; 435/6.14; 435/6.18; 435/7.23; 435/184; 424/9.1

(58) Field of Classification Search
CPC combination set(s) only.
See application file for complete search history.

(56) References Cited

PUBLICATIONS

Daniel K. Nomura et al. Serine Hydrolase KIAA1363: Toxicological and Structural Features with Emphasis on Organophosphate Interactions. Chem. Res. Toxicol. 2006, 19, 1142-1150.*

* cited by examiner

*Primary Examiner* — Kagnew H Gebreyesus
(74) *Attorney, Agent, or Firm* — Hugh Wang; Thomas Fitting; Chad E. Davis

(57) ABSTRACT

A multidimensional profiling strategy that combines activity-based proteomics and metabolomics was used to determine that an active protein, which is a previously uncharacterized enzyme highly elevated in aggressive cancer cells, serves as a central node in an ether lipid signaling network that bridges platelet-activating factor and the lysophospholipids. Biochemical studies confirmed that the active protein regulates this pathway by hydrolyzing the metabolic intermediate 2-acetyl monoalkylglycerol. Inactivation of the active protein disrupted ether lipid metabolism in cancer cells and impaired cell migration and tumor growth in vivo.

6 Claims, 17 Drawing Sheets

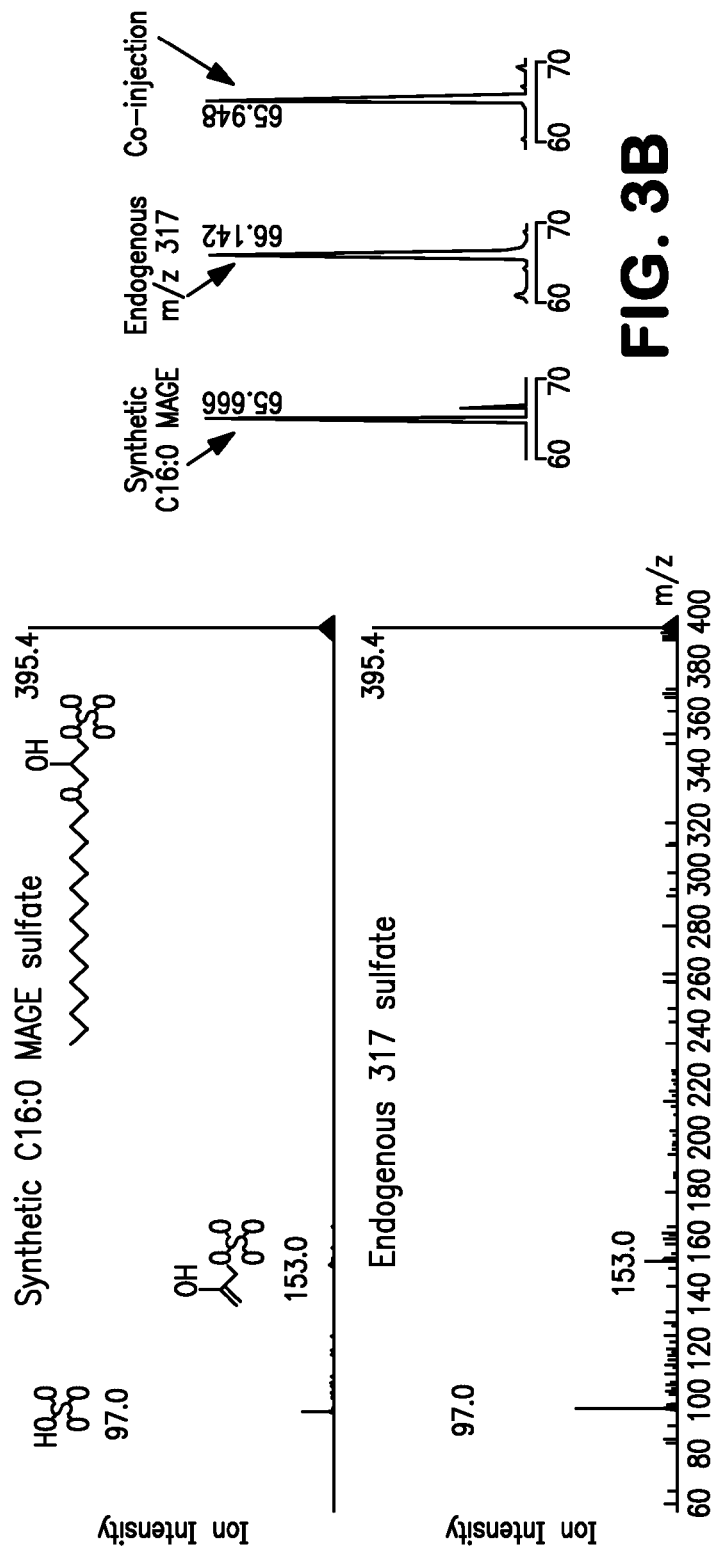

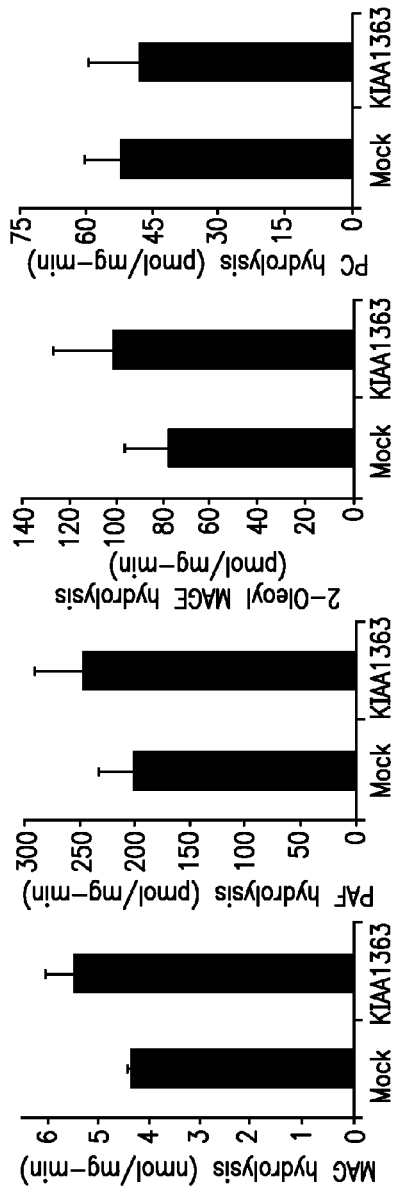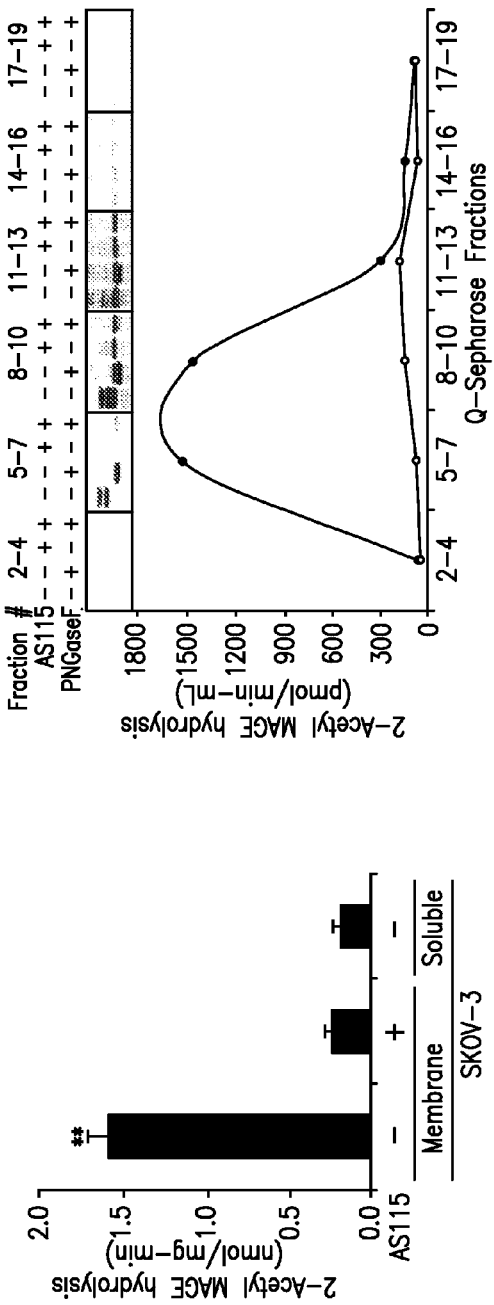
FIG. 6A
FIG. 6B
FIG. 6C

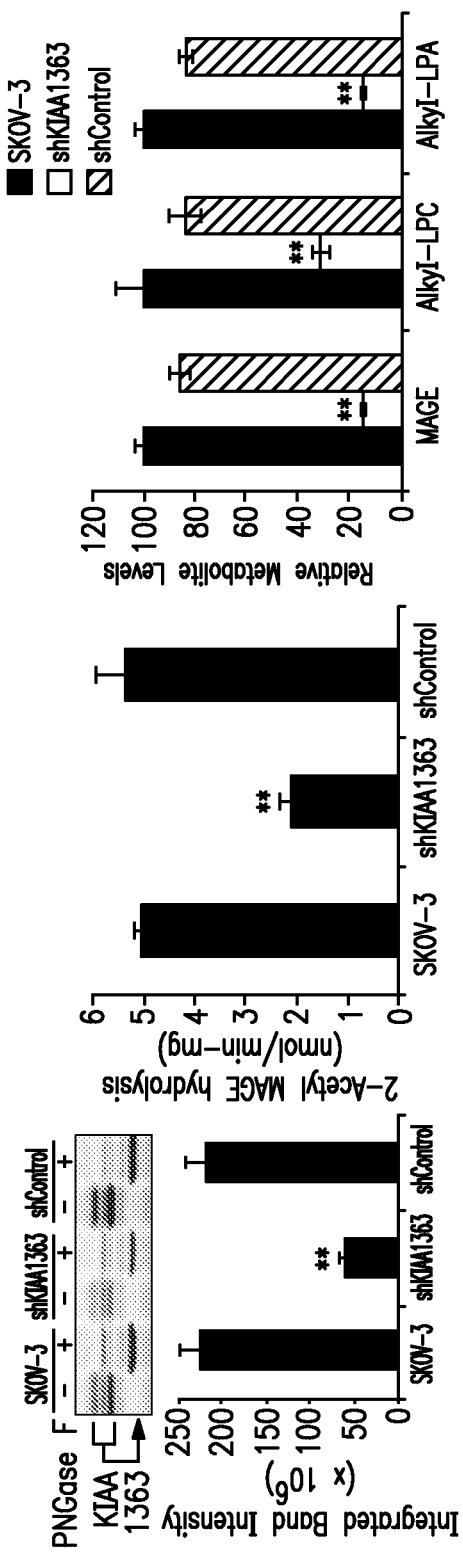

ENZYME REGULATING ETHER LIPID SIGNALING PATHWAYS

STATEMENT OF GOVERNMENT SUPPORT

This invention was made with government support under Grant No. CA087660 awarded by the National institutes of Health. The US. Government has certain rights in the invention.

CROSS REFERENCE TO RELATED APPLICATIONS

This application is a divisional application of U.S. patent application Ser. No. 11/866,349, filed Oct. 2, 2007, now pending; which claims benefit to U.S. Provisional Patent Application Ser. No. 60/849,351, filed Oct. 2, 2006, now abandoned, each of which is incorporated by reference in its entirety.

FIELD OF THE INVENTION

This invention relates generally to proteome analysis and neoplasticity, and more specifically, to the use of serine hydrolase, KIAA1363 to identify tumors and tumor progression, as well as to methods of treatment of cancer by inhibition of this serine hydrolase.

BACKGROUND

The ability to follow intracellular events using a variety of protocols has opened opportunities for identifying the events associated with diseased cells, e.g., hyperplasia and neoplasticity, response to environments, e.g., drugs and other treatments, and the better understanding of the cellular pathways and their interweaving in response to a number of different conditions. By comparing normal cells with diseased cells or cells subjected to a standard environment as compared to a test environment, one can determine how the transcription profile or the proteomic profile has been changed.

In analyzing the proteome of a cell, there are many different categories of cellular components that one can measure: mRNA, proteins, protein locations, protein complexes, modified proteins, etc. Each of these may be varied, depending on the individual, the particular time of the measurement, response to various changes, such as eating, circadian rhythm, stage in proliferation, or other event that may have nothing to do with the status of interest, but may affect the cellular composition. Discovering which proteins have relevance to the cellular status is a significant enterprise. Conventional proteomics approaches that rely on two-dimensional gel electrophoresis encounter difficulties analyzing membrane-associated and low abundance proteins. Additionally, most proteomics technologies are restricted to detecting changes in protein abundance and, therefore, offer only an indirect readout of dynamics in protein activity. Numerous posttranslational forms of protein regulation, including those governed by protein-protein interactions, remain undetected. Each of these posttranslational modifications may have a prominent effect on the status of the cell, where determining only the presence of the protein may be misleading. The large numbers of proteins present in a cell, their dynamic response to changes in the status and environment of the cell, and the changes in the proteins, makes finding correlations between portions of the proteomic profile and useful information concerning disease conditions, response to drugs and useful therapeutic regimes problematic. Thus, the complete understanding of the roles that specific biomolecules play in cell physiology and pathology still presents a challenge, especially for proteins of unknown biochemical or cellular function.

The functions of certain proteins, such as adaptor or scaffolding proteins, can be gleaned from large-scale protein interaction maps generated by technologies like yeast two-hybrid, protein microarrays, and MS analysis of immunoprecipitated protein complexes. In contrast, enzymes contribute to biological processes principally through catalysis. Thus, elucidation of the activities of the many thousands of enzymes encoded by eukaryotic and prokaryotic genomes require knowledge of their endogenous substrates and products. The functional annotation of enzymes in prokaryotic systems has been facilitated by the analysis of gene clusters or operons, which correspond to sets of genes adjacently located in the genome that encode for enzymes participating in the same metabolic cascade. The assembly of eukaryotic enzymes into metabolic pathways is more problematic, however, as their corresponding genes are not, in general, physically organized into operons, but rather are scattered randomly throughout the genome.

Given the absence of a functional architecture connecting eukaryotic genomes and proteomes, the activities of their enzyme constituents are typically assessed in an empirical manner in vitro using candidate substrates and purified preparations of protein. The outcome of these "test-tube" biochemistry studies can be difficult to translate into a clear understanding of the roles that enzymes play in living systems, where these proteins are subjected to post-translational regulation and typically operate as parts of larger metabolic networks.

Development of new targets, biological pathways, and therapeutic agents would be very useful in combating various pathologies. Critical to these developments are efforts to assemble the full complement of characterized and uncharacterized enzymes encoded by the human genome into metabolic and signaling networks that contribute to complex pathologies, like cancer.

In view of the foregoing, an acute need exists to be able to accomplish the determination of endogenous catalytic activities for uncharacterized enzymes directly in living systems, for example, by the integrated application of global profiling technologies that survey both the enzymatic proteome and its primary biochemical output. Embodiments of the present invention provide such uncharacterized enzymes and methods calculated to the determination of their endogenous catalytic activities.

SUMMARY

According to an embodiment of the present invention, a method for identifying a protein associated with the presence of cancer cells is provided, the method comprising identifying an inhibitor, and contacting the inhibitor with the cancer cells under conditions suitable for binding the inhibitor to said protein for determining the identity of endogenous molecules that are regulated by the protein. In one aspect, the inhibitor is identified by methods including, but not limited to, using competitive activity-based protein profiling in a native proteome or substrate based assay for determining a compound that is capable of serving as an inhibitor for the protein.

In one embodiment, the protein has the amino acid sequence SEQ ID NO:2, and the inhibitor comprises the carbamate moiety, such as the compound having the structure:

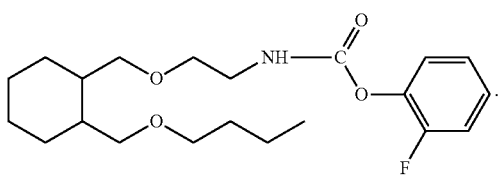 [SMILES: CCCCOCC1CCCCC1COCCNC(=O)Oc1ccccc1F]

According to another embodiment of the present invention, a method for treating a cancer in a patient in need thereof is provided, the method comprising using activity-based protein profiling in for identifying a protein associated with cancer, using competitive activity-based protein profiling in a native proteome for determining a compound that is capable of serving as an inhibitor for the protein, and contacting the inhibitor with the cancer cells, including metastatic cancer cells, under conditions suitable for binding the inhibitor to the protein for treating the cancer.

In one embodiment, a method for treating cancer by modulating lipid signaling pathways in a cell is disclosed including contacting a subject with an agent that modulates the activity or expression of KIAA1363, where KIAA1363 comprises the amino acid sequence as set forth in SEQ ID NO:2 and determining the effect of the agent on cell migration and/or cell growth, proliferation of cancer cells, and/or expression of the oncogenic transcription factor Fra-1, where when KIAA1363 and/or at least one lysophospholipid is elevated in the cell, negatively modulating KIAA1363 activity or expression correlates with a decreased cell migration, and/or cell growth associated with lipid signaling, and/or a decrease in cancer cell growth, and/or a decrease in expression of Fra-1.

In one aspect, the agent is AS115 having the general formula

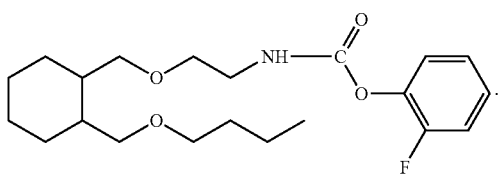

In one embodiment, a method of treating cancer is disclosed including administering to a subject in need thereof a therapeutically effective amount of an inhibitor of KIAA1363, wherein KIAA1363 comprises the amino acid sequence as set forth in SEQ ID NO:2.

In another embodiment, a method of identifying an inhibitor of KIAA1363 is disclosed, including contacting a cell with a nucleic acid encoding an amino acid sequence as set forth in SEQ ID NO: 2, contacting the cells with a first agent, determining the rate of 2-acetyl monoalkylglycerol (MAGE) hydrolysis, or a derivative thereof, for each cell in the presence of the agent, where when the rate of 2-acetyl MAGE hydrolysis decreases in the presence of the first agent, the decrease is indicative of an inhibitory effect of the first agent. In some aspects, at least one control cell with a mock nucleic acid is also used in the method. In a particular aspect, the method may comprise a substrate based assay. For example, such an assay may comprise one or more cells transfected with a vector which tags (e.g., labels) KIAA1363, including, but not limited to FLAG tags and N-terminal tags such as 6×his. Further, such cells may contain one or more selectable markers for determining stable transformants (e.g., including, but not limited to, antibiotic selection markers). Moreover, such assays may comprise isolation of membranes or membrane fractions of the transfected cells. Such assays may include incubating (pre- and/or post inhibitor contact) membranes or cells with one or more protease inhibitors (e.g., PMSF), and/or a —SH group modifiers (e.g., DTNB), which components are contained in an assay buffer comprising one or more detergents, where such detergents are well known in the art (e.g., CHAPS, and the like), and/or DMSO.

In still another embodiment, a further method for identifying an inhibitor of KIAA1363 is provided, including isolating the membrane proteome from cells expressing KIAA1363, contacting the membrane proteome with a thiol-reactive fluorescent reagent and 2-thioacetyl monoalkylglycerol (2-thioacetyl MAGE), in the presence and absence of a test agent under conditions which allow hydrolysis of the 2-thioacetyl MAGE by KIAA1363 and determining the absorbance, wherein a decrease in the absorption in the presence of test compound as compared to the absorbance in the absence of test agent is indicative of an inhibitory effect of the test agent. In one aspect, the thiol-reactive fluorescent reagent is 5,5'-dithiobis-(2-nitrobenzoic acid) (DTNB) and the absorbance is determined at about 405 nm. In some aspects, the cells expressing KIAA1363 are host cells transfected with an expression vector encoding KIAA1363. Such cells may be transiently transfected or stably transfected. Further, such expression vectors may contain one or more selectable markers for determining stable transformants (e.g., including, but not limited to, antibiotic selection markers). Such assays may include incubating membranes with one or more protease inhibitors (e.g., PMSF), which components are contained in an assay buffer comprising one or more detergents, where such detergents are well known in the art (e.g., CHAPS, and the like), and/or DMSO.

In one embodiment, a diagnostic method for determining the presence of KIAA1363 in a cell is disclosed, where KIAA1363 comprises the amino acid sequence as set forth in SEQ ID NO:2 including contacting an agent with a sample, where the agent specifically interacts with a nucleotide encoding SEQ ID NO:2 or an agent which specifically interacts with a peptide or protein comprising the amino acids as set forth in SEQ ID NO:2 and detecting the interaction between the agent and the nucleic acid or peptide, where detection of the interaction is indicative of the presence of KIAA1363 in the sample.

In another embodiment, a kit is disclosed including a device for contacting a biological sample with one or more agents that specifically interact with a nucleotide encoding SEQ ID NO:2 or one or more agents which specifically interact with a peptide or protein comprising the amino acids as set forth in SEQ ID NO:2, instructions which provide procedures on the use of the one or more agents, and a container which houses the one or more agents and instructions.

In one embodiment, a isolated polypeptide is disclosed, including an amino acid sequence as set forth in SEQ ID NO:2.

In another embodiment, an isolated nucleic acid is disclosed, including a sequence encoding SEQ ID NO:2.

In one embodiment, a method for treating cancer by modulating ether lipid signaling in a subject in need thereof is disclosed, including: administering to said subject a therapeutically effective amount of an agent that modulates the activity or expression of KIAA1363, wherein KIAA1363 comprises the amino acid sequence as set forth in SEQ ID NO:2 and determining the effect of said agent on tumor size, tumor progression and/or life expectancy.

BRIEF DESCRIPTION OF THE FIGURES

FIG. 3A shows comparison of the tandem MS fragmentation endogenous and synthetic C16:0 MAGE.

FIG. 3B shows LC migration patterns of endogenous and synthetic C16:0 MAGE.

FIG. 6 shows biochemical characterization of the active protein. A) KIAA1363 transfected COS7 cell extracts lack of hydrolysis of MAG (Left), PAF (left-middle), 2-Oleoyl MAGE (Right-middle) and PC (Right). B) 2-Acetyl MAGE hydrolysis activity predominates in SKOV-3 membrane verus soluble cell extracts. C) 2-Acetyl MAGE hydrolysis activity correlates with KIAA1363 ABPP labeling in Q-separose fractionation of SKOV-3 cell extracts.

FIG. 8 shows metabolic effects of stable shRNA-mediated knockdown of the active protein in human cancer cells. A) shRNA mediated knockdown of KIAA1363 demonstrated by ABPP. B) Reduced 2-Acetyl MAGE hydrolysis activity in KIAA1363 knock down cell extracts. C) Reduction in the endogenous levels of MAGE, LPC, and LPA in KIAA1363 knock down cells.

DETAILED DESCRIPTION OF THE INVENTION

Figure 1:
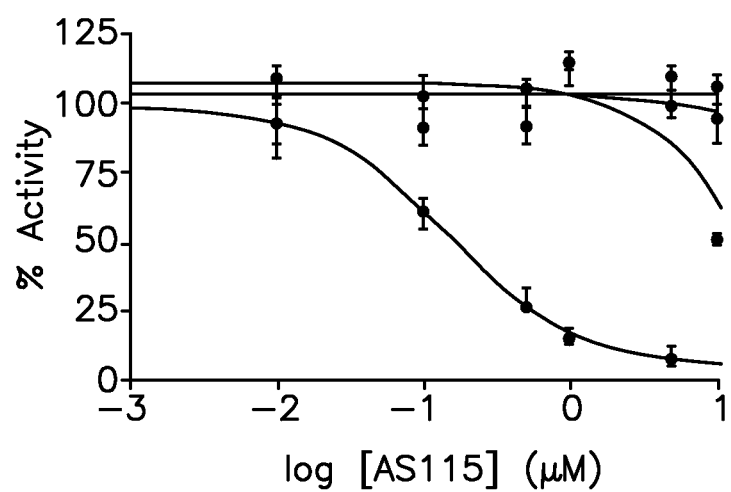
FIG. 1 shows the activity of the AS115 inhibitor.

For the purposes of the present invention, the following terms, definitions and abbreviations apply:

Activity-based probes (ABPs) are provided for specific reaction with the active site of one or more target enzymes, where the target protein is a member of a class of proteins, particularly enzymes, for detection of the presence and quantitation of one or more active members. A single ABP (e.g., but not limited to, a fluorescent labeled ABP or fABP) or mixture of ABPs may be used, where the electrophiles may be different, the environments may be different, including that any attached labels may be different, so as to provide different profiles. The probes may be divided into four characteristics, where the same component may serve two functions and two or more components may together serve a single or multiple functions: (1) a functional group (F) that specifically and covalently bonds to the active site of a protein; (2) a fluorescent label (F1) 3) a linker L, between the F1 and the F; and 4) binding moiety or affinity moiety or label, that may be associated with or part of the linker region and/or the functional group (R) and with serine hydrolases, the binding affinity of the functional group is influenced by the nature of the linker. F and L may be combined to provide an affinity label, as well as the reactive functionality and the linker.

The ABP has an affinity for an enzyme active site, which, while it may be specific for the active site of a particular enzyme, will usually be shared by a plurality of related enzymes.

Exemplary Fs as used in an ABP include an alkylating agent, acylating agent, ketone, aldehyde, sulphonate, photoaffinity or a phosphorylating agent. Examples of particular Fs include, but are not limited to fluorophosphonyl, fluorophosphoryl, fluorosulfonyl, alpha-haloketones or aldehydes or their ketals or acetals, respectively, alpha-haloacyls and nitriles, sulfonated alkyl or aryl thiols, iodoacetylamide group, maleimides, sulfonyl halides and esters, isocyanates, isothiocyanantes, tetrafluorophenyl esters, N-hydroxysuccinimidyl esters, acid halides, acid anhydrides, iminoethers, unsaturated carbonyls or cyano, alkynes, hydroxamates, hemiacetals, alpha-halomethylhydroxamates, aziridines, epoxides, particularly spiroepoxides, azides, or arsenates and their oxides. Sulfonyl groups may include sulfonates, sulfates, sulfinates, sulfamates, etc. in effect, any reactive functionality having a sulfur group bonded to two oxygen atoms. Epoxides may include aliphatic, aralkyl, cycloaliphatic and spiroepoxides, the latter exemplified by fumagillin, which is specific for metalloproteases.

Specificity can be achieved by having groups as part of the active functionality, e.g. sulfonate or sulfate esters, fluorophosphonates, substituted spiroepoxides, etc., where the substituents may be aliphatic, alicyclic, aromatic or heterocyclic or combinations thereof, aliphatically saturated or unsaturated, usually having fewer than 3 sites of unsaturation. Illustrative groups include alkyl, heterocyclic, such as pyridyl, substituted pyridyl, imidazole, pyrrole, thiophene, furan, azole, oxazole, aziridine, etc., aryl, substituted aryl, amino acid or peptidyl, oligonucleotide or carbohydrate group. Many of the functionalities are found in the literature, such as fluorophosphonates, spiroepoxides, sulfonates, olefins, carbonyls, and the like.

ABPs may be illustrated by the following formula:

$$FPO_2\text{-L-FL}$$

where the symbols are:

$FPO_2$ intends fluorophosphonyl;

L is a linker of from 2 to 20, usually 2 to 16, carbon atoms and may be aliphatic, aromatic, alicyclic, heterocyclic or combination thereof, particularly aralkyl, and may include from about 0 to 6 heteroatoms in the chain, e.g. O, S, N and P, such as phenylalkylene, phenylpoly(oxyalkylene), alkylene, poly(oxyalkylene), where the oxyalkylene will usually be of from 2 to 3 carbon atoms; and Fl is an optional fluorescent moiety.

The linker group, while potentially it can be a bond, can be other than a bond. Since in many cases, the synthetic strategy will be able to include a functionalized site for linking, the functionality can be taken advantage of in choosing the linking group. In one aspect, one of skill in the art can select the linker portion of the ABP in order to provide additional specificity of the ABP for a particular enzyme or enzyme class. For example, an alkylene linker and a linker comprising polyethylene glycols ("PEG"), have distinct specificities and provide distinct protein profiles.

Linker groups include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, having from 0 to 3 sites of aliphatic unsaturation. While normally amino acids and oligopeptides are not preferred, when used they will normally employ amino acids of from 2-3 carbon atoms, i.e., glycine and alanine. Aryl groups in linkers can contain one or more heteroatoms (e.g., N, O or S atoms). The linkers, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The atoms are exclusive of hydrogen in referring to the number of atoms in a group, unless indicated otherwise.

Linkers may be varied widely depending on their function, including alkyleneoxy and polyalkyleneoxy groups, where alkylene is of from 2-3 carbon atoms, methylene and polymethylene, polyamide, polyester, and the like, where individual monomers will generally be of from 1 to 6, more usually 1 to 4 carbon atoms. The oligomers will generally have from about 1 to 10, more usually 1 to 8 monomeric units. The monomeric units may be amino acids, both naturally occurring and synthetic, oligonucleotides, both naturally occurring and synthetic, condensation polymer monomeric units and combinations thereof.

The fluorescers may be varied widely depending upon the protocol to be used, their effect on the specificity of the probe, if any, the number of different probes employed in the same assay, whether a single or plurality of lanes are used in the electrophoresis, the availability of excitation and detection devices, and the like. For the most part, the fluorescers that are employed will absorb in the ultraviolet and visible range and emit in the visible and infra red range, particularly emission in the visible range. Absorption will generally be in the range of about 350 to 750 nm and emission will generally be in the range of about 400 to 900 nm. Illustrative fluorophores include xanthene dyes, naphthylamine dyes, coumarins, cyanine dyes and metal chelate dyes, such as fluorescein, rhodamine, rosamine, BODIPY, dansyl, lanthanide cryptates, erbium, terbium and ruthenium chelates, e.g. squarates, and the like. The literature amply describes methods for linking the fluorescers through a wide variety of functional groups to other groups. The fluorescers have functional groups that can be used as sites for linking. The fluorescers that find use will normally be under 2 kDal, usually under 1 kDal.

In some instances, it may be desirable to have a ligand bound to the ABP to allow all of the ABPs, conjugated or unconjugated to be captured and washed free of other components of the reaction mixture. This can be of particular interest where the protein bound to the ABP is partially degraded, leaving an oligopeptide that is specific for the protein and can be analyzed with a mass spectrometer. For mass spectrometry or for other purposes, the ABPs, where the fluorescer may be present or absent, may be labeled with low abundance isotopes, radioactive or non-radioactive. Also, the ligand allows for a cleaner sample to be used for electrophoretic separation, by capture, wash and release. The ligand will generally be under about 1 kDal and biotin is a conventional ligand, particularly analogs such as dethiobiotin and iminobiotin, which can be readily displaced from streptavidin by biotin. However, any small molecule will suffice that can be captured and released under convenient conditions. The ligand will be placed distant from the functional group, generally by a chain of at least about 3 atoms, usually at least about 4 atoms.

An important aspect of this invention is that the probes react with active enzymes. By an "active enzyme" is intended an enzyme, in its normal wild-type conformation, e.g., a catalytically active state, as opposed to an inactive state. The active state allows the enzyme, to function normally. An inactive state may be as a result of denaturation, inhibitor binding, either covalently or non-covalently, mutation, secondary processing, e.g. phosphorylation or dephosphorylation, absence of binding to another protein, etc. Functional states of enzymes as described herein may be distinct from the level of abundance of the same enzymes. An active site is an available wild-type conformation at a site that has biological activity, such as the catalytic site of an enzyme or a cofactor-binding site, or other site where binding of another entity is required to provide catalytic activity. In many instances, one is interested in knowing the level of availability of such sites.

The term "protein" is defined as a biological polymer comprising units derived from amino acids linked via peptide bonds; a protein can be composed of two or more chains.

The term "proteome" is defined as the assembly of all the proteins expressed by a given organism, biological system, tissue or cell at a given time under given conditions. The term "membrane proteome" refers to the assembly of proteins associated with the membranes of cells.

The term "carbamate moiety" is defined as the moiety having the structure (I):

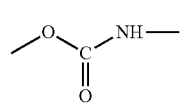

(I)

The term "rhodamine moiety" is defined as the moiety having the structure (II), sometimes abbreviated as "Rh":

(II)

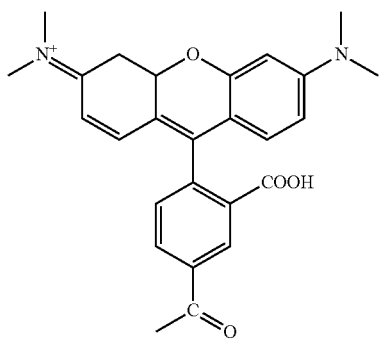

The term "IC$_{50}$" means "inhibitory concentration" and is defined as a concentration of a compound needed to inhibit activity of 50% of an enzyme in a sample.

The following abbreviations are used to explain the multiplicities in the NMR spectra described below in the application: s=singlet, d=doublet, t=triplet, q=quartet, m=multiplet, b=broad.

Methods and compositions are provided concerning enzyme profiles of cells, particularly tumor cells, where the sample being analyzed will usually be from a single source. It is shown that by analyzing for active enzymes in a cell sample, useful information can be derived that can be applied in a number of ways. Cells can be analyzed as to whether they are neoplastic and, if neoplastic, the tumor cells can be evaluated as to their origin, invasiveness or aggressiveness, hormone status for steroid responsive tumors, as well as response to therapy. The cellular contents, which may be fractionated and deglycosylated, are reacted with activity-based probes that preferentially react with the active site of enzymes. The probes have ligands that allow for manipulation of the resulting conjugate for determination and quantitation of the enzyme of the complex.

The methods as described herein provide a way of analyzing cells in relation to their neoplastic condition. The methods employ a single activity based probe or groups of probes that are specific for specific members of a class of enzymes, where the enzymes are found to be up- or down-regulated in their active form based on the nature and the environment of the cells. Using activity-based protein profiling (ABPP), there have been identified enzyme activity signatures that distinguish human cancer cells based on their biological properties, including tumor of origin and state of invasiveness. A primary component of these signatures was thus identified as the active protein (enzyme), herein referred to as "KIAA1363." In one embodiment, KIAA1363 comprises the amino acids as set forth in SEQ ID NO:2.

In one embodiment, a method of identifying the presence of KIAA1363 in a cell is disclosed, where KIAA1363 comprises the amino acid sequence as set forth in SEQ ID NO:2, including obtaining soluble and membranous fractions from the cell, contacting the membrane fraction with a first agent having the general formula:

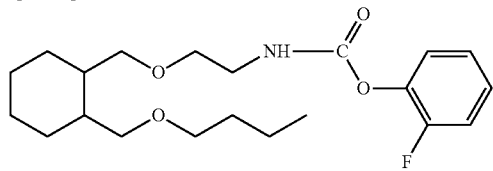

determining the presence or absence of a conjugate between a protein and the agent in the membrane fraction, where determining the presence of a conjugate correlates with the presence of KIAA1363.

KIAA1363 is characterized as a membrane protein having at least two different glycosylated forms with different specificities for neoplastic cells, being upregulated in neoplastic cells. It is found in both breast and melanoma cancer cell lines and is particularly abundant in MUM-2B. The protein is membrane associated, being glycosylated, is an invasive marker when highly glycosylated. It reacts with fluorophosphonate specifically in the active form, regardless of the level of glycosylation. The protein appears to be limited to embryonic cells, cancer cells and the nervous system in its expression profile. As such, it is a desirable marker in that it is absent in most cells in the body and that drugs that cannot cross the blood-brain barrier will not interfere with its function in the nervous system.

Those having ordinary skill in the art can determine a specific procedure to be used for conducting the above-mentioned ABPP. In one embodiment, for example, to conduct the ABPP, native proteomes of interest (e.g. cancer cell proteomes) can be isolated and combined with an activity-based probe (ABP) probe to form an adduct. The active protein of interest can be first isolated, or, if desired, the probe can be combined with the whole proteome sample containing the active protein of interest that is the subject of the analysis and profiling. Any suitable method can be used for the profiling and the analysis. A particular method to be used can be selected by those having ordinary skill in the art. Examples of some analytical or profiling techniques that can be used include fluorescence, labeling and scanning, in-gel visualization, measurement of IC$_{50}$ values, and mass spectrometry. Mass spectroscopy can be used in tandem with microcapillary liquid chromatography-electrospraying.

ABPs are provided for specific reaction with an active site of one or more target proteins in the proteome. The ABPs can comprise at least a reactive functionality and a ligand and have an affinity for a related group of proteins, whereby the ABP can bind to the target protein and substantially inactivate the protein, and the ligand can permit detection and/or isolation, thus profiling the protein of interest. An example of an ABP that can be used is FP-rhodamine. Those skilled in the art can select other appropriate ABPs, if desired. The profiling procedure is described in more detail later in the instant application (see Examples).

After the reaction is completed, the conjugates of the probes and protein targets are analyzed. The probes have a ligand that allows for manipulation of the conjugates, either for sequestering the conjugates or detecting the conjugates or both. The probes may be analyzed by electrophoresis, using gel electrophoresis, capillary electrophoresis or microfluidic electrophoresis, mass spectrometry, e.g., MALDI-TOF, microcapillary liquid chromatography-electrospray tandem MS, or other technique.

A method of competitive ABPP can be used for generating selective inhibitor of the active protein, to determine the role that the active protein plays in cancer cell metabolism and signaling. Because inhibitors in the competitive ABPP procedure are screened against many enzymes in parallel, both potency and selectivity factors can be assigned simultaneously.

A number of techniques can be employed for conducting competitive ABPP. One method that can be used can be directed to the determination of the potency of an inhibitor against an active protein in question. According to this method, for example, an activity-based probe can be combined with KIAA1363 and an inhibitor, under conditions suitable to forming the conjugate. The amount the conjugate present in the sample can be measured.

A control sample can then be made by combining KIAA1363 and the activity-based probe compound without the inhibitor, under conditions suitable to forming the active compound-KIAA1363, and the amount of the KIAA1363 obtained in the control sample can be also measured. The amounts of the KIAA1363 obtained in the first sample and the control sample can then be compared.

In the first sample the inhibitor is expected to bind to a portion of the active protein in question, rendering this portion incapable of reacting with the active compound of the probe. Therefore, a reduction of the signal intensity from the reporter group in the first sample is expected, in comparison with the signal intensity in the control sample. The more potent the inhibitor, the higher degree of reduction is expected. Thus, the potency of the inhibitor can be determined by the reduction of the signal intensity, indicative of the amount of adduct obtained, in a proportion of the quantity of the inhibitor used.

Competitive ABPP screens with a library of candidate inhibitors and a fluorophosphonate (FP) activity-based probe that targets the serine hydrolase superfamily identified a set of trifluoromethyl ketone (TFMK) inhibitors that showed activity against KIAA1363. To enhance the in situ activity of the inhibitors of KIAA1363, the TFMK moiety in the inhibitor can be replaced with a carbamate moiety (I), which inactivates serine hydrolases by a covalent mechanism, as shown by the scheme (III):

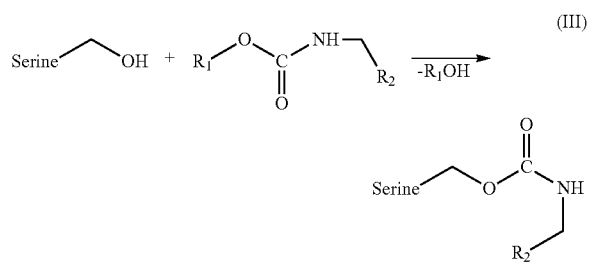

An example of a useful inhibitor having such enhanced in situ activity is inhibitor AS115 having the formula (IV). Those having ordinary skill in the art can select other inhibitors also having a carbamate moiety, if desired.

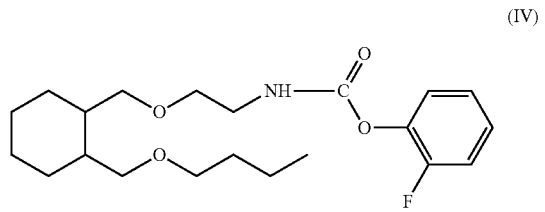 [SMILES: CCCCOCC1CCCCC1COCCNC(=O)Oc1ccccc1F]

Inhibitor AS115 having the formula (IV) was synthesized and tested for its effects on the invasive ovarian cancer cell line SKOV-3 by competitive ABPP with a Rh-tagged FP probe that included moiety (11) shown above. It was determined that AS115 selectively inhibited the active protein in question in aggressive cancer cell lines that possess high levels of this enzyme, including the ovarian cancer line SKOV-3 and the melanoma lines C8161 and MUM-2B. The results are discussed in greater detail in the "Examples" section of the instant application.

The global metabolite profiles of SKOV-3 cells treated with AS115 or vehicle (DMSO) were then compared to identify endogenous small molecules regulated by the active protein. The results are discussed in greater detail in the "Examples" section of the instant application.

Based on the identification of endogenous small molecules regulated by the active protein, the active protein was then biochemically characterized as a 2-acetyl MAGE hydrolase that catalyzes the hydrolysis of 2-acetyl MAGEs to MAGEs. This determination was made in part based on the data provided in the "Examples" section of the instant application.

The conclusion that the active protein is the principal 2-acetyl MAGE hydrolase in cancer cells has been further confirmed. First, 2-acetyl MAGE hydrolase activity was predominantly associated with SKOV-3 membranes as shown on FIG. 6B, where p<0.01 and the shown results represent the average values±standard error for three independent experiments. Additionally, fractionation of the SKOV-3 membrane proteome by Q chromatography revealed a close relationship between levels of the active protein and 2-acetyl MAGE hydrolase activity (FIG. 6C, where white and dark circles represent samples with or without pre-treatment with AS115). Third, SKOV-3 cells possessed much greater 2-acetyl MAGE hydrolase activity compared to the non-invasive ovarian cancer line OVCAR-3 (FIG. 5B), correlating well with their respective levels of the active protein in question.

Figure 7A:
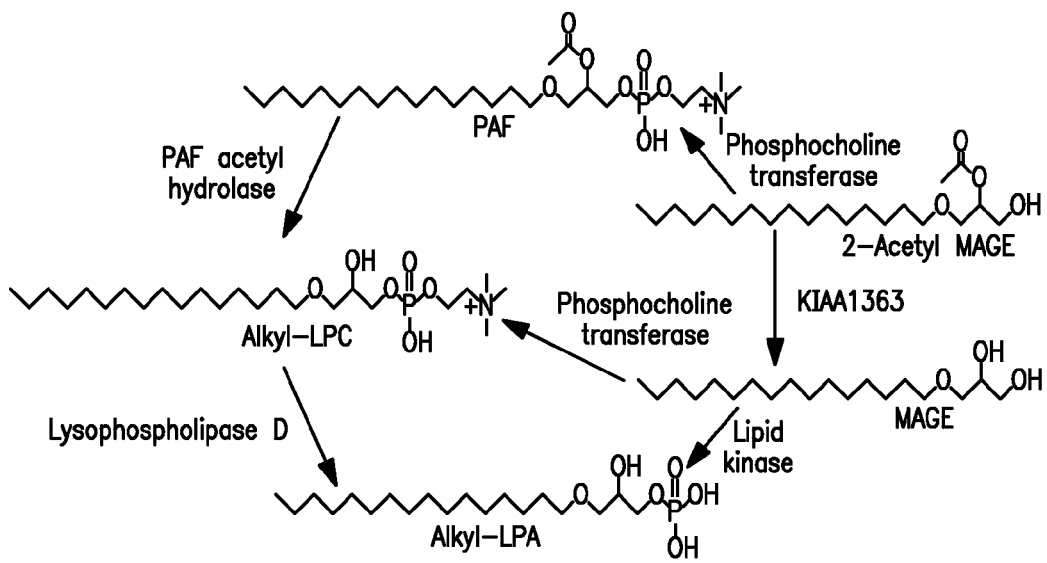
FIG. 7 shows how the active protein can serve as an enzymatic node in a metabolic network that connects the PAF and lysophospholipid families of signaling lipids. A) Network diagram showing metabolites and enzyme components. B) Endogenous MAGE, alkyl-LPC, and alkyl LPA levels in SKOV-3 cell extracts treated are reduced with AS115. C) Accumulation of LPC and LPA by the addition of $^{13}$C-MAGE to SKOV-3 cells. D) Accumulation of PAF in SKOV-3 cells treated with AS115 and $^{13}$C-MAGE. E) MAGE, LPC, and LPA levels are elevated in SKOV-3 cell extracts compared to OVCAR-3 cell extracts.
Figure 7B:
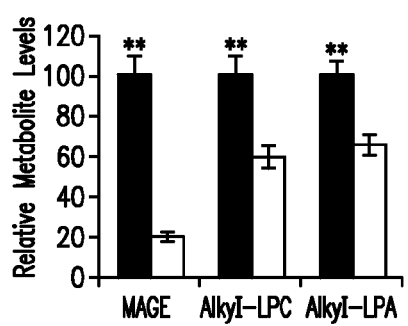
Figure 7C:
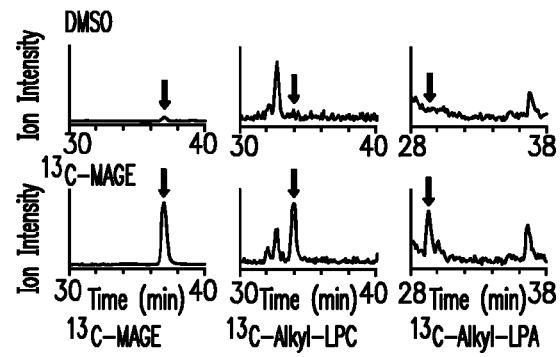
Figure 7D:
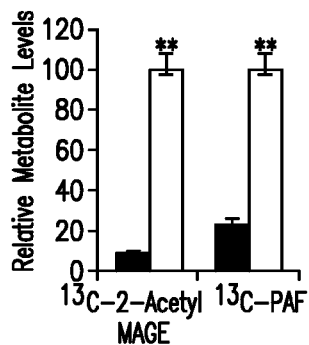
Figure 7E:
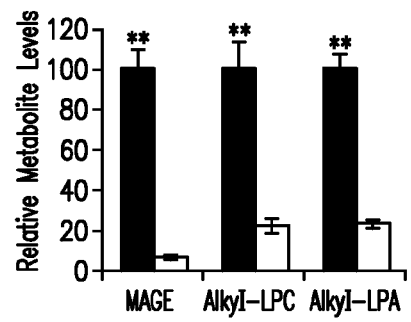

Accordingly, it has been determined that the active protein regulates an ether lipid signaling network that bridges platelet-activating factor (PAF) and the lysophospholipids. In view of the foregoing, those having ordinary skill will understand that the active protein-MAGE pathway might serve as a metabolic node linking the PAF and lysophospholipid signaling systems in cancer cells, as shown by FIG. 7A. This premise can be further tested. To test, the major components of this small-molecule network were measured by targeted LC-MS analysis in AS115- and vehicle-treated SKOV-3 cells. AS115 was found to reduce the levels of not only MAGEs, but also alkyl-LPC and alkyl-LPA (FIG. 7B). Consistent with a direct pathway leading from MAGEs to these lysophospholipids, addition of 13C-MAGE to SKOV-3 cells resulted in the formation of 13C-labeled alkyl-LPC and alkyl-LPA (FIG. 7C).

Conversely, the levels of 2-acetyl MAGE in SKOV-3 cells, as judged by metabolic labeling experiments, were significantly stabilized by treatment with AS115, which in turn led to an accumulation of PAF (FIG. 4D). Basal levels of 2-acetyl MAGE and PAF were not significantly altered by AS115. Finally, a comparison of the metabolite profiles of SKOV-3 and OVCAR-3 cells revealed significantly higher levels of MAGE, alkyl-LPC, and alkyl-LPA in the former line (FIG. 4E). These data indicate that the lysophospholipid branch of the MAGE network is elevated in aggressive cancer cells, and this metabolic shift is regulated by the active protein.

Collectively, these results indicate that KIAA1363 contributes to the pathogenic properties of cancer cells in vitro and in vivo, possibly through regulating the levels of the bioactive lipid LPA.

KIAA1363 can be used as a target for the treatment of cancer. In one embodiment, a method for treating cancer by modulating ether lipid signaling pathways in a cell is disclosed including contacting a subject with an agent that modulates the activity or expression of KIAA1363, where KIAA1363 comprises the amino acid sequence as set forth in SEQ ID NO:2, and determining the effect of the agent on the synthesis of at least one lysophospholipid, cell migration, and/or cell growth, proliferation of cancer cells, and/or expression of the transcription factor Fra-1, where when KIAA1363 and/or at least one lysophospholipid is elevated in the cell, negatively modulating KIAA1363 activity or expression correlates with a decreased level of lysophospholipid, cell migration, and/or cell growth associated with ether lipid signaling, and/or a decrease in cancer cell growth, and/or a decrease in expression of Fra-1.

In a related aspect, "modulate," including grammatical variations thereof, means adjustment or regulation of amplitude, frequency, degree, or activity. In another related aspect, such modulation may be positively modulated (e.g., an increase in amplitude, frequency, degree, or activity) or negatively modulated (e.g., a decrease in amplitude, frequency, degree, or activity).

KIAA1363 can also be used for the preparation of antibodies, both antisera and monoclonal antibodies in accordance with conventional procedures. Mammalian hosts may be immunized with the enzyme, usually in the presence of an adjuvant, employing conventional regimens of injections, waiting 2-4 weeks, bleeding to determine titer, followed by further immunizations to obtain high titer antisera. For monoclonal antibodies, the proteins can be used to immunize mice or other convenient mammalian host, splenocytes isolated and immortalized and the resulting hybridomas screened for affinity for the proteins. These techniques are well known and described in texts. See, for example, Antibodies: A laboratory manual, eds. David Lane and Ed Harlow, Cold Spring Harbor Laboratories, Cold Spring Harbor, N.Y.

KIAA1363 may also be used to prepare labeled derivatives, both fragments and the intact protein, glycosylated and deglycosylated. Various labels may be used, such as fluorescers, radioactive labels, enzyme fragments, particles, molecular dots, etc. The methods for conjugating labels to KIAA1363 are well known in the literature and need not be described here.

These proteins are readily purified to at least about 50% purity (based on total protein), usually at least about 75% purity, and desirably at least about 90% purity to totally pure, using one or more conventional methods for protein purification, such as SDS-PAGE, liquid chromatography, particularly HPLC, or capillary electrophoresis.

The protein of the present invention serves as a target for determining candidate compounds possessing inhibitory activity against KIAA1363. Various techniques can be used for evaluating candidate compounds. In one aspect, one may use the probes as competitors for the candidate compound for binding to the active site of the enzyme. By combining the enzyme, the probe, and the candidate compound in an appropriately buffered medium, one determines the change in conjugate formation in the presence and absence of the candidate compound. Alternatively, one may combine the candidate compound and enzyme substrate with the enzyme and determine the change in turnover in the presence and absence of the candidate compound.

In one embodiment, a method of identifying an inhibitor of KIAA1363 is disclosed including contacting a cell with a nucleic acid encoding an amino acid sequence as set forth in SEQ ID NO: 2 and at least one control cell with a mock nucleic acid, contacting the cells with a first agent, determining the rate of 2-acetyl monoalkylglycerol (MAGE) hydrolysis, or a derivative thereof, for each cell in the presence of the agent, where when the rate of 2-acetyl MAGE hydrolysis decreases in the presence of the first agent, the decrease is indicative of an inhibitory effect of the first agent. Other techniques may also be used, as appropriate. In one aspect, the method may comprise a substrate based assay. For example, such an assay may comprise one or more cells transfected with a vector which tags (i.e., labels) KIAA1363, including, but not limited to FLAG tags and N-terminal tags such as 6×his. Further, such cells may contain one or more selectable markers for determining stable transformants (e.g., including, but not limited to, antibiotic selection markers). Moreover, such assays may comprise isolation of membranes or membrane fractions of the transfected cells. Such assays may include incubating (pre- and/or post inhibitor contact) membranes or cells with one or more protease inhibitors (e.g., PMSF), and/or a —SH group modifiers (e.g., DTNB), which components are contained in an assay buffer comprising one or more detergents, where such detergents are well known in the art (e.g., CHAPS, and the like), and/or DMSO.

In another aspect, there is provided a further method for identifying an inhibitor of KIAA1363, including isolating the membrane proteome from cells expressing KIAA1363, contacting the membrane proteome with a thiol-reactive fluorescent reagent and 2-thioacetyl monoalkylglycerol (2-thioacetyl MAGE), in the presence and absence of a test agent under conditions which allow hydrolysis of the 2-thioacetyl MAGE by KIAA1363 and determining the absorbance, wherein a decrease in the absorption in the presence of test compound as compared to the absorbance in the absence of test agent is indicative of an inhibitory effect of the test agent.

The term "thiol-reactive fluorescent reagent" as used herein refers to a compound that reacts with thiol to produce fluorescence. Such reagents may be used to monitor the hydrolysis of KIAA1363 substrates in the methods disclosed herein. Examples of these reagents are well-known in the art (see e.g., *The Handbook—A Guide to Fluorescent Probes and Labeling Technologies*, 10th Edition, Chapter 2, Web Edition, hosted by Invitrogen, Inc., Carlsbad, Calif.) and include iodoacetamides, maleimides, coumarin derivatives, and bimanes. Particular examples include monobromobimane, monochlorobimane, 7-diethylamino-3-(4'-maleimidylphenyl)-4-methylcoumarin (CPM), Hg-link Alexa Flour 350 phenylmercury reagent (Invitrogen, Inc.), and 5-(bromomethyl) fluorescein. In a preferred embodiment, the thiol-reactive fluorescent reagent is 5,5'-dithiobis-(2-nitrobenzoic acid) (DTNB) and the absorbance is determined at about 405 nm.

In some aspects, the cells expressing KIAA1363 are host cells transfected with an expression vector encoding KIAA1363. Such cells may be transiently transfected or stably transfected. Further, such expression vectors may contain one or more selectable markers for determining stable transformants (e.g., including, but not limited to, antibiotic selection markers). Expression vectors may further contain nucleic acid sequences encoding amino acid sequences (e.g., 6×His tag or FLAG tag) for tagging the N-terminus or C-terminus of the KIAA1363 protein. In preferred embodiments the host cells may be 293T cells or COS-7 cells. Such assays may include incubating membranes with one or more protease inhibitors (e.g., PMSF), which components are contained in an assay buffer comprising one or more detergents, where such detergents are well known in the art (e.g. CHAPS, and the like), and/or DMSO.

In another embodiment, a method of treating cancer is disclosed including administering to a subject a therapeutically effective amount of an inhibitor of KIAA1363. Such inhibitors include, but are not limited to, antibodies, nucleic acids, and small molecules.

In one aspect, nucleic acids include antisense nucleic acids, short hairpin RNAs, siRNA, and ribozymes. Methods of synthesizing nucleic acid molecules are known in the art. In one aspect, for example, such nucleic acids can be produced by methods as described in Verma and Eckstein (1998).

The nucleic acids can also be prepared b) enzymatic transcription from synthetic DNA templates or from DNA plasmids isolated from recombinant bacteria. Typically, for RNAs, phage RNA polymerases are used such as T7, T3 or SP6 RNA polymerase (Milligan and Uhlenbeck (1989)).

A further aspect of the present invention relates to a method of mediating target-specific KIAA1363 modulation, for example by RNA interference.

In a related aspect, the RNA molecule is transduced into a target cell, e.g., an isolated target cell, e.g., in cell culture, a unicellular microorganism or a target cell or a plurality of target cells within a multicellular organism. In another aspect, transduction may include carrier-mediated delivery, e.g. by liposomal carriers or by injection.

The nucleic acids of the present invention may be used for determining the function of a gene in a cell or an organism including modulating the function of a gene in a cell or an organism. In one aspect, the cell is a eukaryotic cell or a cell line, e.g., an animal cell, including, but not limited to, a tumor cell, e.g. a melanoma cell, a breast cancer cell, and a pancreatic cell. In another aspect, the organism is a eukaryotic organism, e.g., an animal, such as a mammal, including a human.

In one embodiment, nucleic acids of the present invention are directed to modulate KIAA1363 which is associated with a pathological condition (e.g., cancer). By modulating KIAA1363, particularly, by inhibiting the function of KIAA1363 therapeutic benefits, may be obtained.

A nucleic acid of the present invention can be administered as a pharmaceutical composition. The administration may be carried out by known methods, where a nucleic acid is introduced into a desired target cell in vitro or in vivo. Commonly used gene transfer techniques include calcium phosphate, DEAE-dextran, electroporation and microinjection and viral methods (Graham, F. L. and van der Eb, A. J. (1973) Virol. 52, 456; McCutchan, J. H. and Pagano, J. S. (1968), J. Natl. Cancer Inst. 41, 351; Chu, G. et al (1987), Nucl. Acids Res. 15, 1311; Fraley, R. et al. (1980), J. Biol. Chem. 255, 10431; Capecchi, M. R. (1980), Cell 22, 479). An additional technique for the introduction of nucleic acids into cells is the use of cationic liposomes (Feigner, P. L. et al. (1987), Proc. Natl. Acad. Sci. USA 84, 7413). Commercially available cationic lipid formulations are e.g. Tfx 50 (Promega) or Lipofectamin2000 (Life Technologies). In one aspect, multiple nucleic acids can be generated for the same target.

Thus, the invention also relates to a pharmaceutical composition containing as an active agent at least one nucleic acid molecule, antibody, and/or small molecule as described above and a pharmaceutical carrier. The composition may be used for diagnostic and for therapeutic applications in humans.

For diagnostic or therapeutic applications, a therapeutic agent/composition may be in the form of a solution, e.g., an injectable solution, a cream, ointment, tablet, suspension or the like. The composition may be administered in any suitable way, e.g., by injection, by oral, topical, nasal, rectal application, and the like. The carrier may be any suitable pharmaceutical carrier. In one aspect, a carrier is used, which is capable of increasing the efficacy of the agent/composition to enter the target-cells. Suitable examples of such carriers are liposomes, including cationic liposomes. In another aspect, administration is carried out by injection.

In one embodiment, a diagnostic method for determining the presence of KIAA1363 in a cell is disclosed, where KIAA1363 comprises the amino acid sequence as set forth in SEQ ID NO:2, including contacting an agent with a sample, wherein the agent specifically interacts with a nucleotide encoding SEQ ID NO:2 or an agent which specifically interacts with a peptide or protein comprising the amino acids as set forth in SEQ ID NO:2, and detecting the interaction between the agent and the nucleic acid or peptide, where detection of the interaction is indicative of the presence of KIAA1363 in the sample. In one aspect, the agent is an antibody. Agent interactions further include ligands that recognize moieties which are bound covalently or non-covalently to the antibody. For example, an antibody may be labeled with a biotin moiety, and the reagent would then comprise streptavidin. Other ligands useful for this purpose are known in the art.

Suitable labels for the antibodies of the present invention are provided below. Examples of suitable enzyme labels include malate dehydrogenase, staphylococcal nuclease, 4005-15, 2000). Avidin-enriched FP-labeled proteins were separated by SDS-PAGE and the protein bands excised, digested with trypsin, and the resulting peptides analyzed by a combination of matrix assisted laser desorption mass spectrometry (MS)[Voyager-Elite time-of-flight MS instrument (PerSeptive Biosystems)] and microcapillary liquid chromatography-electrospray tandem MS (Agilent 1100 HPLC combined with a Finnigan LCQ MS).

The protein band gel pieces were cut into several small pieces and destained with MeOH, washed with 100 mM ammonium bicarbonate in 30% acetonitrile a few times, then digested with trypsin (100 ng) in 3 mM Tris-HCl at pH 8, 37° C. over night. The tryptic peptides were extracted out of the gel using 50% acetonitrile/0.1% TFA, concentrated to 10 μl, and subjected to Nano-LCMS to be analysis.

Nano-Capillary HPLC-Tandem Mass Spectrometry (MS/MS):

The nano-LCMS/MS experiment was performed on a combination system of Agilent 1100 capillary HPLC/Micro Auto-sampler (Agilent Technologies. Palo Alto, Calif.) and Finnigan LCQ DecaXP ion trap mass spectrometer (Finnigan, San Jose, Calif.).

LC Separation:

A 3 μl of digested sample was mixed with 3 μl of 5% Acetic Acid and loaded on a 100 μm fused silica capillary $C_{18}$ column. A sixty-minutes gradient of 5-95% solvent B (A: $H_2O$/ 0.1% Formic Acid, B: MeCN/0.08% Formic Acid) and a 500 nl/min column flow rate was used to separate the tryptic peptides in the digested sample. Peptides eluted out from the column were directly injected into LCQ DecaXP mass spectrometer to be analyzed.

Mass Spectrometry:

The heated desolvation capillary in the mass spectrometer was held at 200° C., the spray voltage was set at 2.0 kV and the capillary voltage was set at 30 V. During the experiment, the mass spectrometer was set to alternate between MS and MS/MS mode. The scan range for MS was set at m/z 400-1600. The MS/MS spectra were acquired in dependent scan mode with an initiating minimum MS signal at $2 \times 10^3$ counts, and a 35% normalized collision energy. The scan range for MS/MS is varied from 80-2000 depending on the precursor ion.

Protein Identification:

The ion masses and the fragmentation information generated by nano-LCMS/MS experiment were analyzed and converted into peptide masses and sequence information with TurboSEQUEST, which is protein identification software. With this program, searching against the protein database with that information from the spectra then identified proteins.

Characterization of a Membrane-Associated Serine Hydrolase KIAA1363 as a Marker for Cancer Cell Invasiveness.

The up-regulation of KIAA1363 in invasive cancer lines suggested that this enzyme may represent a new marker of tumor progression as well as a target for therapeutic modalities. Consistent with these notions, database searches revealed that the gene encoding KIAA1363 localizes to 3q26, a chromosomal region highly amplified in a variety of malignant cancers, including nearly 50% of advanced stage ovarian tumors. To further explore the relationship between KIAA1363 activity and cancer cell invasiveness, the levels of activity of this enzyme was determined across a panel of human ovarian cancer lines and correlated these values with measurements of invasiveness.

Figure 12A:
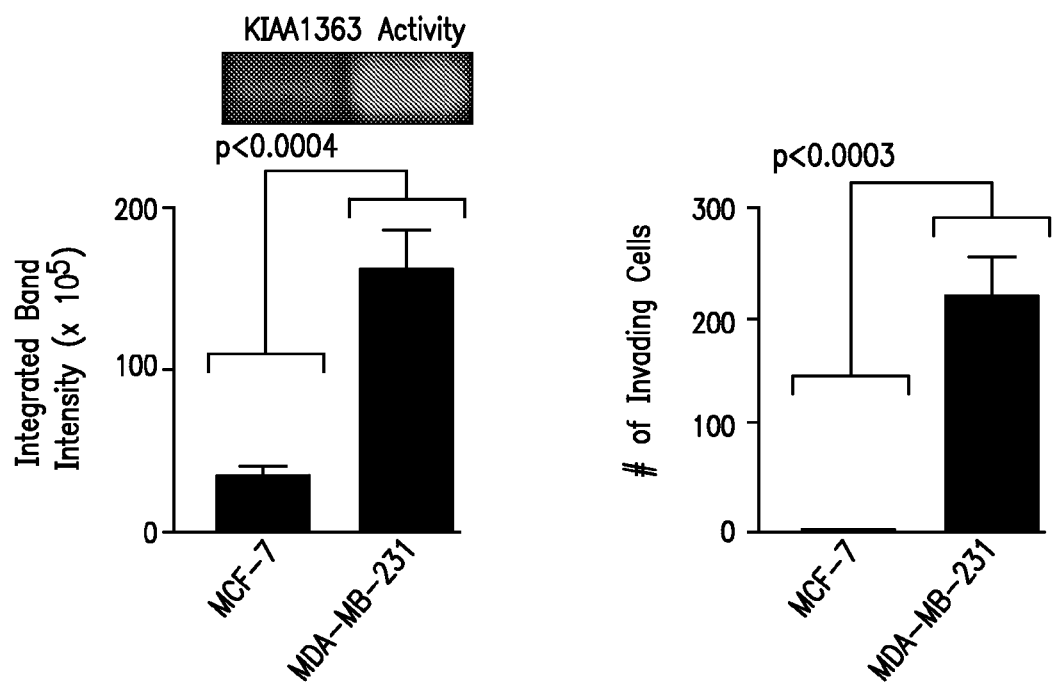
FIGS. 12A-12C shows the correlation between the activity of the membrane-associated hydrolase KIAA1363 and the invasiveness of human cancer cell lines. (A-C) Levels of active KIAA1363 present in cancer cell membrane proteomes as measured by ABPP (Left), and cancer cell invasiveness as measured by matrigel invasion assays (Right). Results expressed as number of invading cells refers to average number of invading cells per 8 fields counted (n=3-4 for each cell line). (A) Breast carcinoma lines. (B) Melanoma lines. (C) Ovarian carcinoma lines.
Figure 12B:
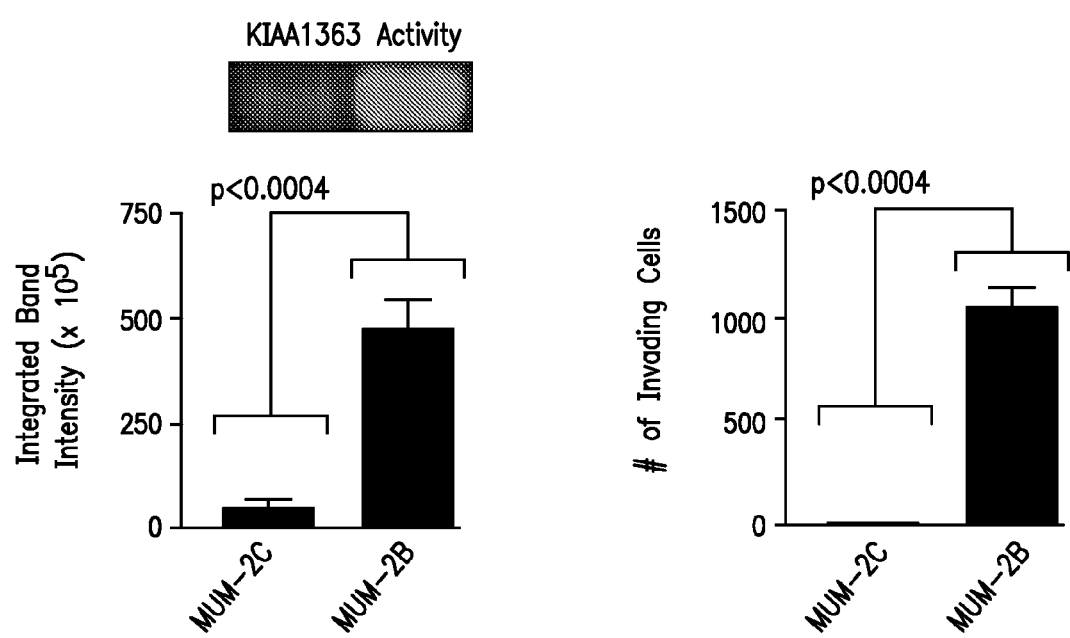
Figure 12C:
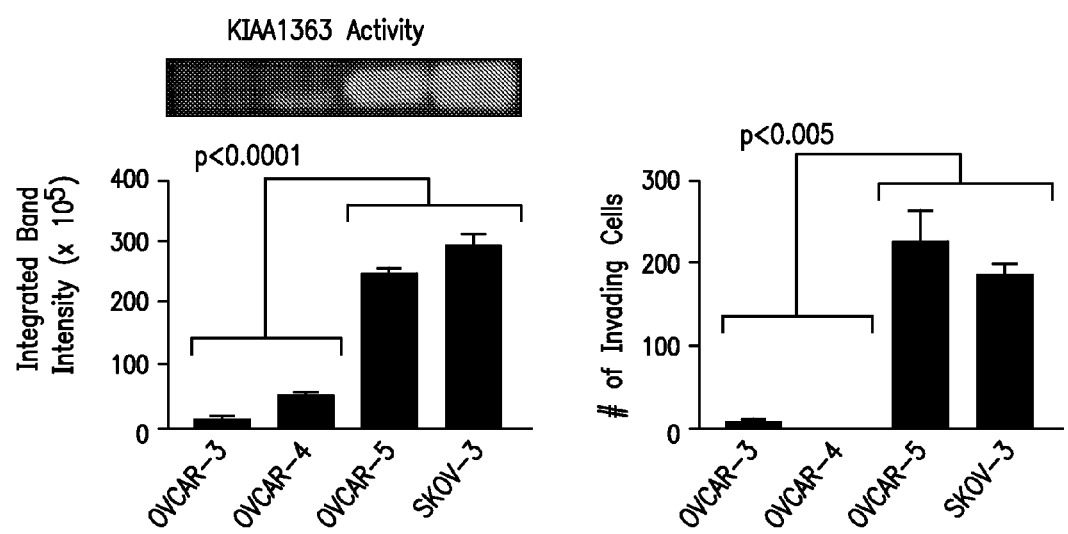

A group of four ovarian carcinoma lines were selected that, despite forming a discrete cluster based on global gene expression profiles, were otherwise relatively uncharacterized in terms of their cell biological properties, including invasiveness. The strong positive correlation observed between the levels of active KIAA1363 and cell invasiveness in breast carcinoma (FIG. 12A) and melanoma (FIG. 12B) lines directly extended to the ovarian carcinoma lines (FIG. 12C). Specifically, the two ovarian carcinoma lines that displayed high invasiveness (OVCAR-5, SKOV-3) were found to exhibit 5- to 25-fold higher levels of active KIAA1363 than the two noninvasive ovarian carcinoma lines (OVCAR-3, OVCAR-4). Thus, activity levels of the membrane-associated enzyme KIAA1363 correlated with pronounced differences in the invasiveness of cell lines derived from three distinct types of cancer, even in a case where this cellular phenotype was not reflected at the level of global gene expression profiles.

The reactivity of SAE with FP-rhodamine, coupled with the enzyme's ability to hydrolyze esterified sialic acid groups, suggested that the KIAA1363 was a member of the serine hydrolase superfamily.

C17:0 lysophosphatidic acid (LPA), C16:0 2-acetyl MAGE, PAF, and phosphtidylcholine were purchased from Avanti Lipids. C15:0 monoacylglycerol (MAG) was purchased from Larodan (Sweden). FP-rhodamine was synthesized following known procedures. Synthesis of $^{13}$C-C16:0 MAGE and targeted acetylation to generate $^{13}$C-C16:0 2-acetyl MAGE were carried out also as known. Human construct of the active protein in question was generated by PCR using the following primers: 5'-CGCGGATCCATGAG-GTCGTCCTGTGTCCTG-3' (SEQ ID NO:3) and 5'-12 CGGAATTCTTACAGGTTTTGATCTAGCC-3' (SEQ ID NO:4). PCR products were subcloned into the pcDNA3.1+ vector (Invitrogen) using BamHI and EcoRI restriction sites.

The following LC-MS conditions were used for analysis of cancer cell metabolomes. Cell pellets were harvested by scraping, isolated by centrifugation at 1,400×g, and dounce-homogenized in 4 mL of a 2:1:1 mixture of chloroform: methanol:Tris buffer (50 mM Tris*HCl, pH 8.0). Samples that were analyzed by targeted LC-MS were homogenized in the presence of the following synthetic standards: C15:0 MAG (50 pmol), C17:0 LPA (50 pmol), and 13C-C16:0 MAGE (25 pmol). Organic and aqueous layers were separated by centrifugation at 1,260×g for 5 min. The organic layer was then removed, dried under a stream of N2, and re-solubilized in 100 μL of chloroform, of which 30 μL was analyzed by LC-MS. Extraction of LPA was performed by acidifying the remaining aqueous layer to a final concentration of 5% formic acid, followed by the addition of 2 mL of chloroform. The mixture was vortexed, the organic layer removed, concentrated to dryness, and dissolved in 100 μL of chloroform, of which 30 μL was analyzed by LC-MS.

LC-MS analysis was performed using an Agilent 1100 LC-MSD SL instrument. LC-separation was achieved with a Gemini reverse phase $C_{18}$ column (5 μm, 4.6 mm×50 mm) from Phenomonex together with a precolumn ($C_{1B}$, 3.5 μm, 2 mm×20 mm). Mobile phase A was composed of a 95:5 ratio of water:methanol and mobile phase B consisted of 2-propanol, methanol, and water in a 60:35:5 ratio. Solvent modifiers such as 0.1% formic acid and 0.1% ammonium hydroxide were used to assist ion formation as well as improve the LC resolution in both positive and negative ionization modes respectively. The flow rate for each run started at 0.1 mL/min for 5 min, to alleviate backpressure associated with injecting chloroform. The gradient started at 0% B and increased linearly to 100% B over the course of 40 min with a flow rate of 0.4 mL/min, followed by an isocratic gradient of 100% B for 7 min before equilibrating for 8 min at 0% B with a flow rate of 0.5 mL/min.

MS analysis was performed with an electrospray ionization (ESI) source. The capillary voltage was set to 3.0 kV and the fragmentor voltage to 100V. The drying gas temperature was 350° C., the drying gas flow rate was 10 L/min, and the nebulizer pressure was 35 psi. Untargeted data was collected using a mass range of 200-1000 Da and exported as common data format (.CDF) files for computational analysis. Differentially expressed metabolites between sample pairs were identified using the XCMS analyte profiling software (http://metlin/download) that aligns mass peaks from two LC-MS traces and quantifies the relative intensities of global metabolites (5). Significant inhibitor-sensitive peak changes were confirmed by manual quantification using the area under the peak normalized to total ion current. Targeted LC-MS measurements were made using selected ion monitoring (SIM). Peaks were quantified by measuring the area under the peak and normalized to an internal standard (C15:0 MAG) or endogenous lipid (palmitic acid). Absolute MAGE levels were estimated by comparison to a 13C-MAGE standard.

Example 1

Synthesis of AS115

This example shows one way of preparing the inhibitor AS115, according to the synthetic scheme (V) shown below:

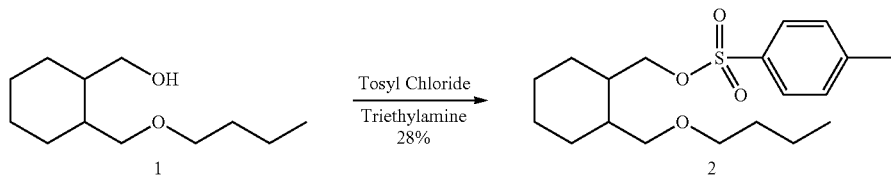

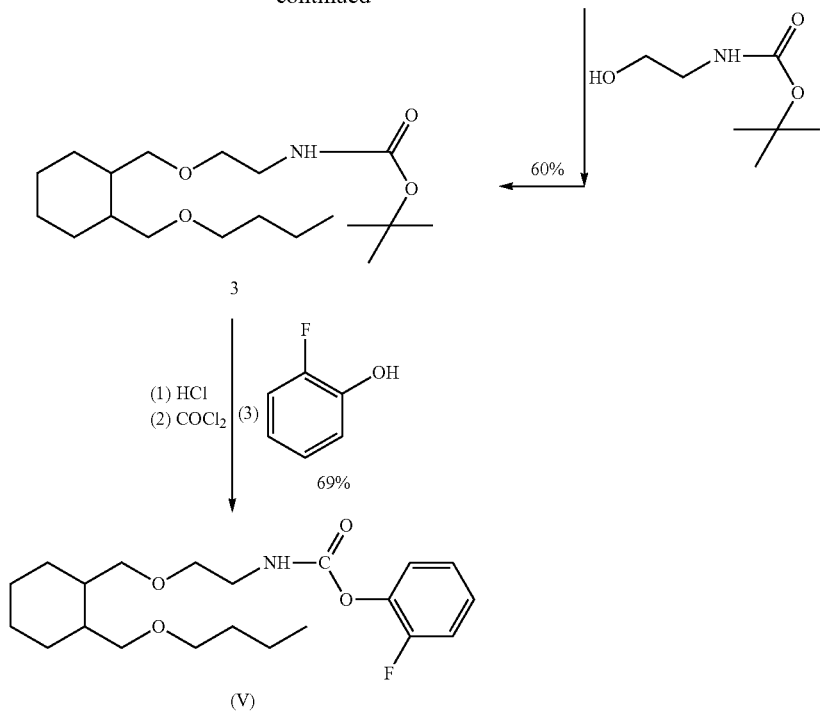

To the alcohol 1 (200 mg, 1 mmole, 1 eq.) in 5 mL of CH$_2$Cl$_2$ was added tosyl chloride (285 mg, 1.5 mmole, 1.5 eq.) and triethylamine (287 mL, 2 mmole, 2 eq.). The reaction was stirred overnight at 4° C. and then washed sequentially with saturated ammonium chloride, water, and brine. The organic layer was then isolated dried with sodium sulfate and concentrated. The intermediate 2 shown on scheme (V) was isolated as a clear oil (100 mg, 28% yield) after chromatography on silica gel (EtOAc:Hexanes, 5:95 v/v).

Next, the tosylate intermediate 2 (100 mg, 0.28 mmole, 1 eq.), BOC-ethanolamine (137 mg, 0.85 mmole, 3 eq.) and CsCO$_3$ (299 mg, 0.85 mmole, 3 eq.) were refluxed in CH$_2$Cl$_2$ (5 mL) overnight. The reaction was diluted with EtOAc (20 mL) and washed with water (20 mL). The organic layer was then isolated dried with sodium sulfate and concentrated. The intermediate 3 was isolated as a clear oil (56 mg, 60% yield) after chromatography on silica gel (EtOAc:Hexanes, 10:90 v/v).

The final product, AS115, was then obtained as follows. The BOC-protected intermediate 3 in methanol (2 mL) was treated with 4 M HCl solution in dioxane (2 mL) for 2 hours. The reaction was then concentrated and placed under high vacuum for an additional hour. The amine was then dissolved with saturated sodium bicarbonate (2 mL) and CH$_2$Cl$_2$ (2 mL) and stirred vigorously while being cooled to 0° C. Once cooled, phosgene as a 20% solution in toluene (250 mL) was added to the organic layer and the solution was stirred vigorously for an additional 15 minutes. The mixture was diluted with CH$_2$Cl$_2$ and water (5 mL each) and the organic layer was separated from the aqueous layer and dried with sodium sulfate. The organic layer containing the isocyanate was then concentrated and taken forward to the next reaction. To the freshly prepared isocyanate in toluene (3 mL) was added 2-fluorophenol (9.3 mL, 0.10 mmole, 0.95 eq) and triethylamine (30 mL, 0.22 mmole, 2 eq). The mixture was stirred overnight at 80° C. The reaction was then concentrated and directly purified by flash chromatography (EtOAc:Hexanes, 15:85 v/v) to afford AS115 as a colorless oil (26 mg, 69% for all steps).

The final product, AS115, was characterized as follows. TLC (EtOAc:Hexanes, 20:80 v/v): RF=0.64; $^1$H-NMR (400 MHz, CDCl$_3$): δ 7.2631-7.1091 p.p.m. (m, 4H), 5.7099 (s, 1H), 3.5817-3.2949 (m, 10H), 2.0204-2.0108 (m, 2H), 1.6823-1.3310 (m, 12H), 0.9240-0.8874 (t, J=7.32 Hz, 3H); $^{13}$C-NMR (125 MHz, CDCl$_3$): δ 155.9, 153.7, 138.6, 126.5, 124.1, 116.5, 71.7, 70.9, 69.2, 41.3, 37.2, 31.8, 27.3, 26.6, 23.6, 19.4, 13.9; HRMS (m/z): [M]+ calculated for C$_2$H$_{32}$FNNaO4. 404.2213. Found, 404.2206.

Example 2

In Situ Inhibition of the Active Protein in Cancer Cells

Human ovarian cancer cell lines were obtained form the National Cancer Institute's Developmental Therapeutics Program. The melanoma lines C8161 and MUM-2B were obtained form Mary Hendrix. Cells were maintained in RPMI medium 1640 with 10% (v/v) fetal calf serum at 37° C. in a humidified atmosphere of 5% CO2/95% air. At approximately 80% confluency, cells were trypsinized, counted with the aid of a hemocytometer, and 2.5×106 cells were plated in 6 cm dishes. 20 h after plating cells were washed twice with PBS and supplemented with serum free RPMI containing 0.5% BSA (Sigma)(BSA-RPMI) with AS115 (0.01-10 µM) or vehicle (DMSO) at 0.1%. After incubation for 4 h the cells were harvested and analyzed by ABPP or LC-MS.

In-gel fluorescence scanning of FP-labeled proteomes derived from SKOV-3 cells treated in culture with AS115 (0-10 µM) revealed selective inactivation of the active protein which migrates by SDS-PAGE as a 43 and 45 kDa glycosylated doublet, which, upon treatment with PNGaseF, is converted into a single 40 kDa protein. Inhibitor AS115 displayed an $IC_{50}$ value of 150 nM, while other serine hydrolase activities were not affected by this agent ($IC_{50}$ values>10 μM), as shown by FIG. 1. Inhibitor AS115 also selectively inhibited the active protein in other aggressive cancer cell lines that possess high levels of this enzyme, including the melanoma lines C8161 and MUM-2B.

Example 3

Identification of Endogenous Small Molecules Regulated by the Active Protein

Figure 2A:
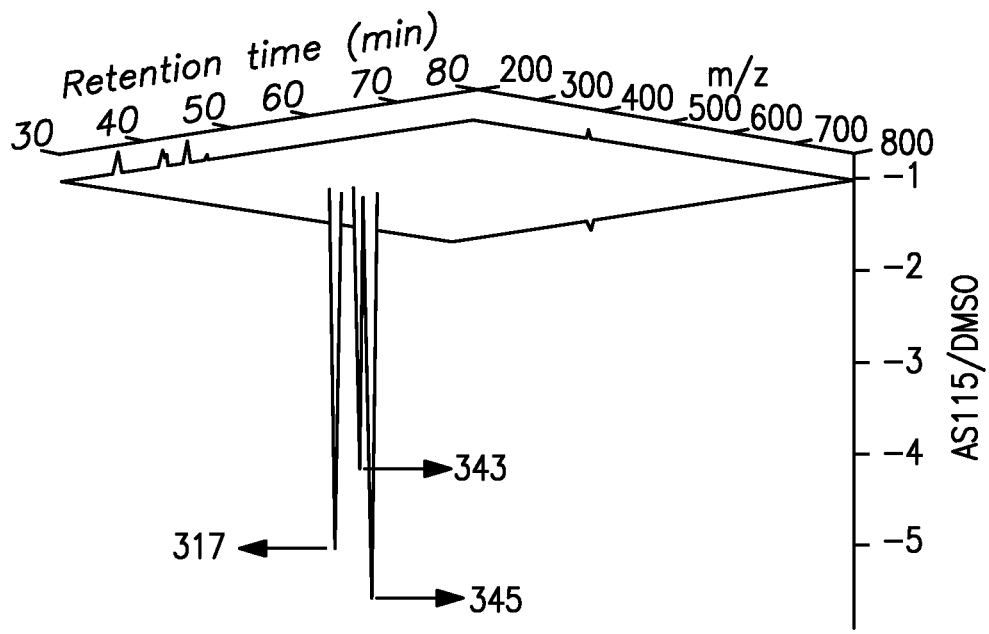
FIG. 2A shows the global metabolite profiles of SKOV-3 cells treated with AS115 or vehicle (DMSO).

These experiments were performed using the method of untargeted liquid chromatography-mass spectrometry (LC-MS) for comparative metabolomics. Cells were treated with AS115 (10 μM) or DMSO for 4 h and analyzed by untargeted LC-MS methods. AS115 was found to cause a substantial reduction in the levels of a specific set of lipophilic metabolites (m/z 317, 345, and 347) in SKOV-3 cells, as shown by FIG. 2A. Relative mass signals are shown in Table 1, represented as the average values and standard error for three independent experiments. Only MAGEs were found to change significantly in level as a result of AS115 treatment (p<0.001).

TABLE 1

Relative Mass Signals For Representative Lipid Metabolites in DMSO- And AS115-Treated SKOV-3 Cells

| Lipid Class Acyl Chain | DMSO/AS115 SKOV-3 Cells | p-value |
|---|---|---|
| FFA | | |
| C14 | 0.69 | 0.253 |
| C16 | 0.69 | 0.218 |
| C18:1 | 0.56 | 0.160 |
| C18 | 0.76 | 0.148 |
| C20:4 | 1.04 | 0.805 |
| PA | | |
| C32 | 1.01 | 0.96 |
| C34:1 | 0.95 | 0.695 |
| C34 | 1.41 | 0.137 |
| C36:2 | 0.74 | 0.021 |
| C36:1 | 0.99 | 0.961 |
| PE | | |
| C32 | 1.13 | 0.745 |
| C34:1 | 0.84 | 0.379 |
| C34 | 0.94 | 0.709 |
| C36:2 | 0.61 | 0.248 |
| C36:1 | 0.94 | 0.653 |
| PS | | |
| C32 | 1.06 | 0.808 |
| C34:1 | 0.96 | 0.862 |
| C34 | 1.02 | 0.944 |
| C36:2 | 1.13 | 0.656 |
| C36:1 | 0.99 | 0.951 |
| PC | | |
| C32 | 1.07 | 0.408 |
| C34:1 | 1.01 | 0.976 |
| C34 | 0.96 | 0.851 |
| C36:2 | 1.07 | 0.851 |
| C36:1 | 0.68 | 0.415 |
| PG | | |
| C32 | 0.78 | 0.617 |
| C34:1 | 0.98 | 0.910 |
| C34 | 0.95 | 0.798 |
| C36:2 | 1.04 | 0.846 |
| C36:1 | 0.89 | 0.617 |

TABLE 1-continued

Relative Mass Signals For Representative Lipid Metabolites in DMSO- And AS115-Treated SKOV-3 Cells

| Lipid Class Acyl Chain | DMSO/AS115 SKOV-3 Cells | p-value |
|---|---|---|
| Ceramide | | |
| C16 | 0.53 | 0.557 |
| C18 | 0.73 | 0.161 |
| MAG | | |
| C16 | 1.00 | 0.972 |
| C18:1 | 0.83 | 0.420 |
| MAGE | | |
| C16 | 5.29 | <0.001 |
| C18:1 | 4.42 | <0.001 |
| C18 | 5.86 | <0.001 |

The above-discussed m/z 317, 345, and 347 metabolites regulated by the active protein did not correspond to any of the typical lipid species found in cells, including free fatty acids, phospholipids, ceramides, and monoacylglycerides, none of which were significantly altered by AS115 treatment.

Figure 2B:
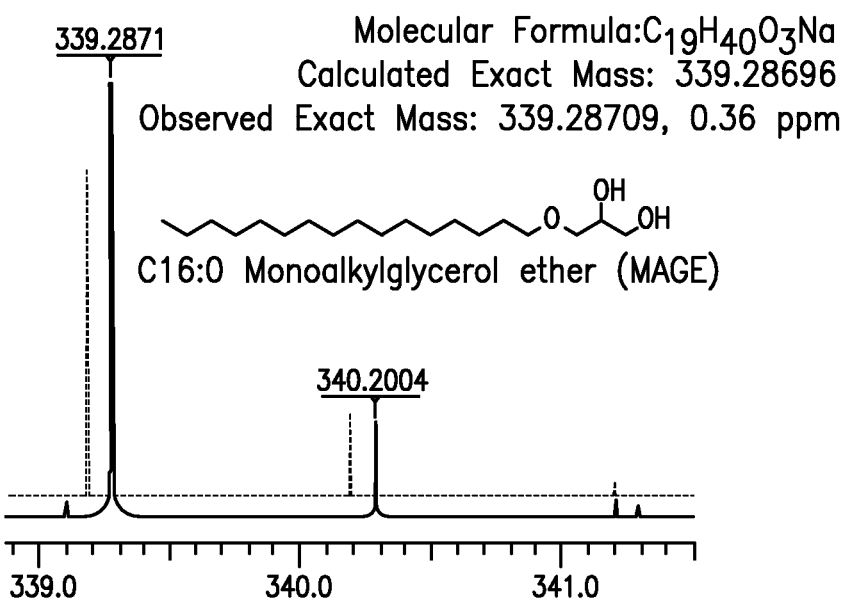
FIG. 2B shows a high-resolution mass spectrum of the m/z 317 lipophilic metabolite.

High-resolution MS of the m/z 317 metabolite provided a molecular formula of $C_{19}H_{40}O_3$, as shown by FIG. 2B, which suggested that this compound might represent a monoalkylglycerol ether bearing a C16:0 alkyl chain (C16:0 MAGE). This structure assignment was corroborated by tandem MS and LC analysis, where the endogenous m/z 317 product and synthetic C16:0 MAGE displayed equivalent fragmentation and migration patterns, respectively, as shown by FIGS. 3A and 3B. The data shown by FIGS. 3A and 3B are for endogenous C16:0 MAGE purified from SKOV-3 cell extracts. The endogenous and synthetic C16:0 MAGE samples showed equivalent MS fragmentation patterns (generated with sulfate-derivatized products to enhance fragmentation) and co-migrated by LC.

By extension, the m/z 345 and 347 metabolites were interpreted to represent the C18:1 and C18:0 MAGEs, respectively. Targeted LC-MS analysis provides estimates of the absolute levels of MAGEs in SKOV-3 cells, revealing that the C16:0 species was the most abundant member of this lipid family, as shown in Table 2. MAGE levels were measured by targeted LC-MS analysis of SKOV-3 cells treated with AS115 (5 μM) or DMSO for 4 h using a 13C-C16:0 MAGE internal standard. Values are represented as pmol/$10^6$ cells. Results represent the average values and standard error for three independent experiments.

TABLE 2

Absolute Levels of MAGE Lipids in SKOV-3 cells

| | MAGE Lipids (pmol/$10^6$ cells) | | |
|---|---|---|---|
| AS115/DMSO | C16:0 | C18:0 | C18:1 |
| AS115 | 19.3 ± 2.2 | 7.6 ± 2.3 | 4.0 ± 0.7 |
| DMSO | 94.7 ± 6.6[*] | 39.5 ± 3.7[*] | 12.1 ± 0.4[*] |

[*] p < 0.01 for AS115 vs. DMSO-treated samples

Figure 4:
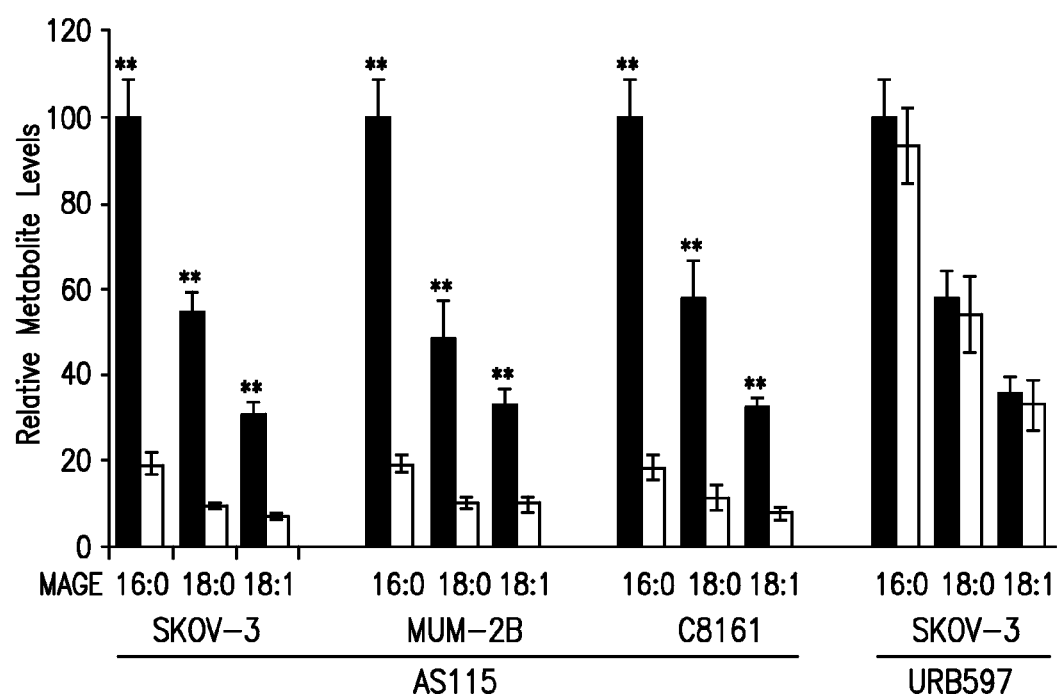
FIG. 4 shows comparison of the effects of AS115 and a control carbamate URB597 on the active protein and MAGE levels in cancer cells.

MAGE lipids were also significantly reduced in C8161 and MUM-213 melanoma cells following treatment with AS115 as shown by FIG. 4. In contrast, a control carbamate inhibitor, URB597, which targets other hydrolytic enzymes, but not the active protein, did not affect MAGE levels in cancer cells (FIG. 4). On FIG. 4, white bars signify the inhibitor-treated samples and black bars signify the DMSO-treated samples, and p<0.01. The results represent the average values and standard error for three independent experiments. As can be seen from FIG. 4, AS115, but not URB597 significantly lowered the levels of MAGE lipids in both ovarian (SKOV-3) and melanoma (MUM-2B, C8161) cancer lines compared to DMSO controls.

Example 4

ABPP Analysis of Cancer Cell Proteomes

Cells were washed twice and scraped in ice-cold PBS. Cell pellets were isolated by centrifugation at 1,400×g for 3 min and dounce-homogenized in Tris buffer. Membrane proteomes were isolated by centrifugation at 4° C. at 100,000×g to provide a soluble fraction and a particulate fraction (pellet). The pellet was washed and resuspended in Tris buffer by sonication to provide a membrane fraction. Proteomes protein concentrations were determined by a protein assay kit (Bio-Rad), adjusted to a final concentration of 1 mg/mL in Tris buffer, and treated with 2 μM FP-rhodamine for 30 min at room temperature (50 μL total reaction volume). After labeling, a portion of each sample was treated with PNGaseF (New England Biolabs) to provide deglycosylated proteomes. Reactions were quenched with one volume of standard 2×SDS/PAGE loading buffer (reducing), separated by SDS/PAGE (10% acrylamide) and visualized in-gel with a Hitachi FMBio Ile flatbed fluorescence scanner (MiraiBio). Integrated band intensities were calculated for the labeled proteins and averaged from 3 independent cell samples to determine the level of each enzyme activity. IC50 values were determined from dose-response curves from three trials at each inhibitor concentration using Prism software (GraphPad) to obtain values with 95% confidence intervals.

Example 5

Characterization the Active Protein as a 2-acetyl MAGE Hydrolase

Figure 5A:
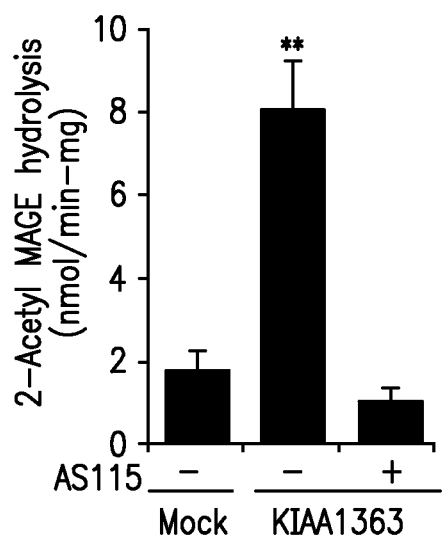
FIG. 5 shows determination of the active protein as a 2-acetyl MAGE hydrolase. A) 2-Acetyl MAGE hydrolysis activity in KIAA1363 transfected COS7 cell extracts and mock transfected cell extracts. KIAA1363 transfected cell extracts were also treated with AS115. B) 2-Acetyl MAGE hydrolysis activity in extracts of ovarian cancer cell lines OVCAR-3 and SKOV-3 either mock or treated with AS115.
Figure 5B:
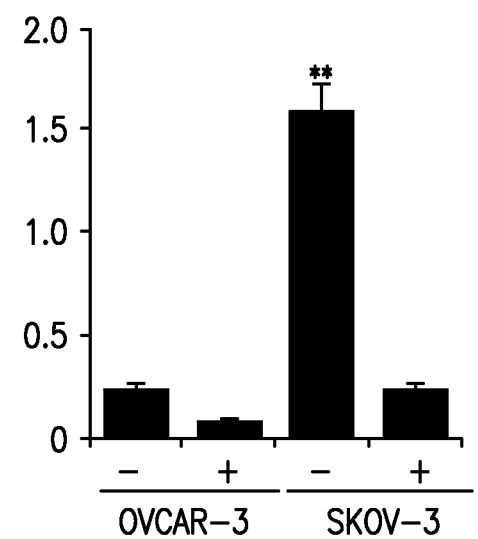

The enzyme in question was transiently transfected into COS7 cells, and so transfected cells possessed significantly higher 2-acetyl MAGE hydrolase activity compared to mock-transfected cells and this elevated activity was blocked by treatment with AS115, as shown by FIG. 5A (p<0.01). As can be seen from FIG. 5A, COS7 cells transiently transfected with the active protein's cDNA in the pcDNA3 expression vector showed significantly greater 2-acetyl MAGE hydrolase activity compared to mock-transfected cells (transfected with empty pcDNA3 vector). Pre-treatment with AS115 (10 μM) blocked the hydrolytic activity of the active protein-transfected cells. In contrast, the active protein- and mock-transfected cells showed no differences in their respective hydrolytic activity for 2-oleoyl MAGE, monoacylglycerols, or phospholipids (e.g., platelet-activating factor (PAF), phosphatidylcholine) (see FIG. 6A).

Example 6

Preparative HPLC Purification of C16:0 MAGE

Large-scale preparations of cultured SKOV-3 cells (~4× 107 cells) were plated in 10×15 cm dishes and incubated in serum-free media for 48 hours. Cells pellets were isolated as described above and homogenized in 8 mL of 2:1:1 mixture of chloroform:methanol:Tris buffer. The organic layer was removed, dried under a stream of N2, and resolubilzed in 200 L of chloroform. The metabolite extracts were LC purified using a Hitachi L-7150 HPLC system equipped with a semi-preparative C18 reverse phase column (5 μm, 10 mm×50 mm) from Phenomonex.

Fractions, one per minute, were collected using a Gilson FC 203B fraction collector. Fractions containing the 317 metabolite were identified by MS analysis, collected, extracted with chloroform, concentrated to dryness, and the residue was then dissolved in a minimal amount of solvent B (200-300 μL) for exact mass analysis.

Example 7

Metabolic Labeling of SKOV-3 Cells with 13C-2-acetyl MAGE and 13C-MAGE

Cells were cultured and maintained as described above. Cells used for 13C-2-acetyl MAGE experiments were incubated in BSA-RPMI containing inhibitor or vehicle for min. BSA-RPMI medium was then removed, supplemented with 10 μM 13C-2-acetyl MAGE or DMSO, and re-applied to cells. After incubation for 1 h the cells were harvested and metabolomes were analyzed by LC-MS. 13C-MAGE experiments were conducted by addition of 13C-MAGE or DMSO containing BSA-RPMI directly after washing with PBS. Cells were then incubated for 4 h, harvested, and analyzed by LC-MS.

Example 8

Fourier Transform Mass Spectrometry (FTMS) Experiments

High-accuracy measurements were performed in the positive ion mode using a Bruker (Billerica, Mass.) APEX III (4.7 T) FTMS instrument equipped with an Apollo electrospray source. The collected LC fractions were mixed with a collection of small molecule standards and directly infused at 3 μL/min using a Harvard Apparatus (Holliston, Mass.) syringe pump. Pneumatic assist at a backing pressure of 60 psi was used along with an optimized flow rate of heated counter-current drying gas (300° C.). Ion accumulation was performed using SideKick without pulsed gas trapping. Data acquisition times of approximately 17 min were used, yielding a resolving power of ~130000 at m/z 446 in broadband in the m/z range of 200-2200. Calculated molecular masses for ions generated by a mixture of small molecule standards were used to internally calibrated the data.

Example 9

Sulfonation of C6:0 MAGE

To a 4 mL vial with a magnetic stir bar were added endogenous HPLC purified C16:0 MAGE or synthetic standard (Sigma) and 1% (w/v) sulfur trioxide in 4:1 dimethylformamide and pyridine. This mixture was stirred at 70° C. for 2 h. The reaction mixture was then concentrated to dryness under a stream of nitrogen followed by 1 h under vacuum, and the residue was then dissolved in a minimal amount of methanol for MS/MS analysis.

Example 10

Tandem MS Experiments

MS/MS experiments were performed in the negative ion mode using a Micromass QTof-Micro™ (Manchester, U.K.)

instrument equipped with a Z-spray electrospray source and a lockmass sprayer. The source temperature was set to 110 C with a cone gas flow of 150 L/h, a desolvation gas temperature of 365° C., and a nebulization gas flow rate of 350 L/h. The capillary voltage was set a 3.2 kV and the cone voltage at 30 V. The collision energy was set at 15-35 V. Samples were directly infused using at 4 µL/min using a Harvard Apparatus syringe pump. MS/MS data were collected in the centroid mode of over a scan range of m/z 70-450 for acquisition times of 2 min.

Example 11

Enzyme Activity Assays With Lipid Substrates

Membrane and soluble proteomes were adjusted to 0.25 mg/mL in Tris buffer and pre-incubated with AS115 (10 mM) or DMSO for 15 min. Lipid substrates (2-acetyl MAGE, 2-oleoyl MAGE, phosphatidylcholine, PAF) were assayed at 100 µM in 100 µL of proteome at room temperature for various amounts of time (5-40 min), after which reactions were quenched with 200 µL of chloroform and 50 µl methanol. Lipid substrates and products were extracted into the organic layer, concentrated to dryness, and resolubilized in 300 µL of chloroform prior to LC-MS analysis. MS settings, columns, and mobile phases were similar to those described above. Hydrolysis products were quantified by measuring the area under the peak in comparison to standard curves generated with purified products. Specific activity was determined during the linear phase of enzymatic reactions (i.e., less than 20% product observed). Monoacylglycerol hydrolysis was measured using a 14C-labeled 2-oleoylglycerol substrate following the conversion to 14C-oleic acid using a thin layer chromatography assay. For enzyme assays performed with recombinant KIAA1363, COS7 cells were transiently transfected with the human KIAA1363 cDNA in the mammalian expression vector pcDNA3 following known methods.

Example 12

Q Chromatography Enrichment of the Active Protein

Cell membranes were isolated as described above and solubilized by rotating for 1 h at 4° C. in Tris buffer containing 1% Triton X-100. Detergent insoluble proteins were removed by centrifugation at 100,000×g for 45 min. Triton-solubilized proteomes were adjusted to a final protein concentration of 1 mg/ml- and subjected to anion-exchange chromatography in Tris buffer with 0.1% Triton X-100 on a Q Sepharose HP column (Amersham Pharmacia Biotech) using a 10 min linear gradient of 0-1 M NaCl at a flow rate of 0.5 mL/min. Fractions were pooled, tested for 2-acetyl MAGE hydrolytic activity, and analyzed by FP-rhodamine as described above.

Example 13

Western Blotting With Anti-Active Protein Polyclonal Antibodies

A KIAA1363-GST fusion protein was generated by subcloning human active protein into the pGEX4T-3 fusion vector (Amersham Pharmacia Biotech) using BamH1 and EcoRI restriction sites. Rabbit polyclonal antibodies were raised against KIAA1363-GST fusion protein, expressed in E. coli BL21 strain according to manufacturer's recommendations (Amersham Pharmacia Biotech), administered in conjunction with RIBI adjuvant (Corixa). Affinity purification of the anti-KIAA1363 antibodies was conducted by first depleting rabbit antiserum of GST-cross reactive antibodies followed by isolation of KIAA1363-GST reactive antibodies form the remaining serum as previously described (7). Western blotting analysis was performed with known anti-KIAA1363 polyclonal antibodies.

Example 14

Preparation of a Xenograft Tumor-Derived SKOV-3 Line

In vivo-derived SKOV-3 lines were established following known procedures. Briefly, a well-established SKOV-3 xenograft tumor growing in the mouse flank was removed aseptically and minced with a razor blade; tumor pieces were transferred into tissue culture flasks with complete medium. After 4 days of culture, when abundant adherent tumor cells were visible, floating tumor debris was removed. Attached cells were then expanded to constitute a propagatable cell population.

Example 15

RNA Interference Studies in Human Cancer Cell Lines

RNA interference studies were conducted using a variant of the SKOV3 line isolated by in vivo passaging in immune-deficient mice. This in vivo-derived SKOV3 line showed enhanced tumor-forming capacity in vive compared to the parental line, as is known to those skilled in the art. Short hairpin RNA constructs were subcloned into the pLP-RetroQ acceptor system and retrovirus was generated using the AmphoPack™-293 Cell Line (Clontech). Hairpin oligonucleotides utilized were: for KIAA1363, 5' TGT GAA CAC CCC AAT CCT G 3' (SEQ ID NO:5); for DPPIV, 5' GAT TCT TCT GGG ACT GCT G 3' (SEQ ID NO:6). A pLP-RetroQ vector was developed for tPa using a validated oligonucleotide sequence purchased from Clontech. Virus containing supernatant from 24-72 h was collected, concentrated by ultracentrifugation and in the presence of 10 µg/ml polybrene used to stably infect SKOV-3 cells for 48 h. Infection was followed by 3 days of selection in medium containing 1 µg/ml of puromycin as the retroviral vector contained this selection marker. Infected SKOV-3 cells were expanded and tested for the loss of enzyme activity by ABPP.

Example 16

Tumor Xenograft Studies

Human cancer xenografts were established by transplanting cancer cell lines ectopically into the flank (SKOV-3) or mammary fat pad (231 mfp) of C.B17 SCID mice (Taconic Farms). Briefly, cells were washed two times with PBS, trypsinized, and resuspended in medium containing serum. Next, the harvested cells were washed two times with serum-free medium and resuspended at a concentration of 4.4×104 cells/µl (or 1.0×104 cells/L for 231 mfp cells) and 1001 were injected. Growth of the tumors was measured every three days with calipers.

Example 17

Cell Migration Assay

Migration assays were performed in Transwell chambers with 8 μM pore-sized membranes coated with 10 μg/ml collagen overnight at 4° C. (Corning). Twenty-four hours before the start of the migration assay, cancer cell lines were plated at concentration of 2.25×106 cells per 10 cm dish. At the start of the migration assay, cells were harvested by washing two times with PBS and then serum starved in medium containing 0.05% BSA for 4 hours. Serum starved cells were trypsinized, spun at 1400 rpm for 3 minutes, resuspended, and counted. Cells were diluted to a density of 100,000 cells/ml in medium contain 0.05% BSA, and then 250 μl were placed in the upper chamber of the transwells. Either DMSO, alkyl LPA (10 nM), alkyl LPC (10-1000 nM), or MAGE (10-1000 nM) in medium containing 0.05% BSA was added in the lower chamber, and cells were allowed to migrate for 18 h. The filters were then fixed and stained with Diff-Quik (Dade Behring). Cells that had not migrated through the chamber were removed with a cotton ball. The cells which migrated were counted at a magnification of 40× and from each migration chamber 6 fields were independently counted.

Example 18

Cell Proliferation Assay

Cancer cell lines were plated at a concentration of 6.4×105, 3.2×105, 1.6×105, 8×104 cells per 10 cm dish in triplicate. They were then counted two, four, six, and eight days after plating with trypan blue (Sigma).

Example 19

Determination of the Impairment of the Tumor Growth In Vivo

Figure 9A:
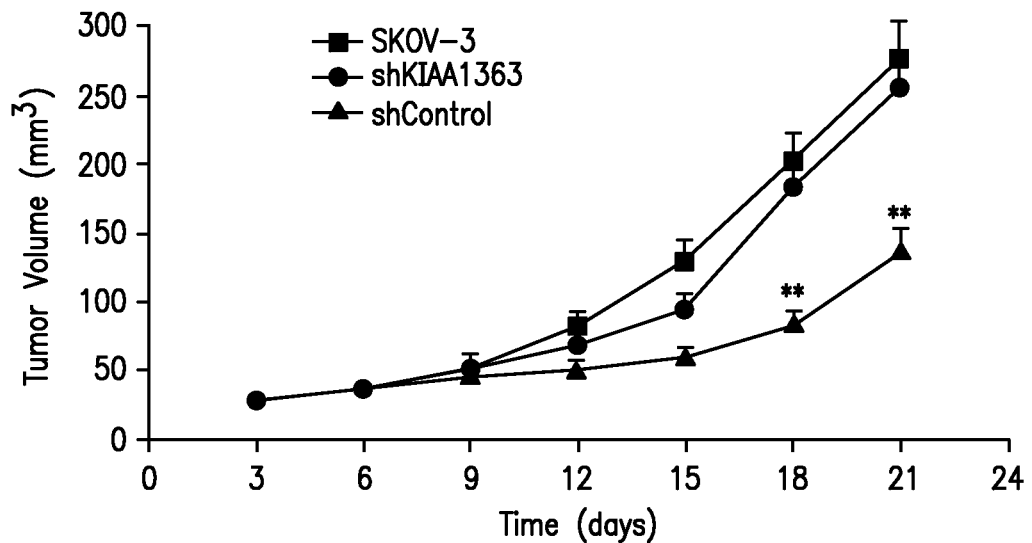
FIG. 9 shows contribution of the active protein to ovarian tumor growth and cancer cell migration. A) KIAA1363 knockdown cells show reduced tumor growth in vivo. B) KIAA1363 knockdown cells show reduced migration potential which is rescued by the addition of LPA.
Figure 10A:
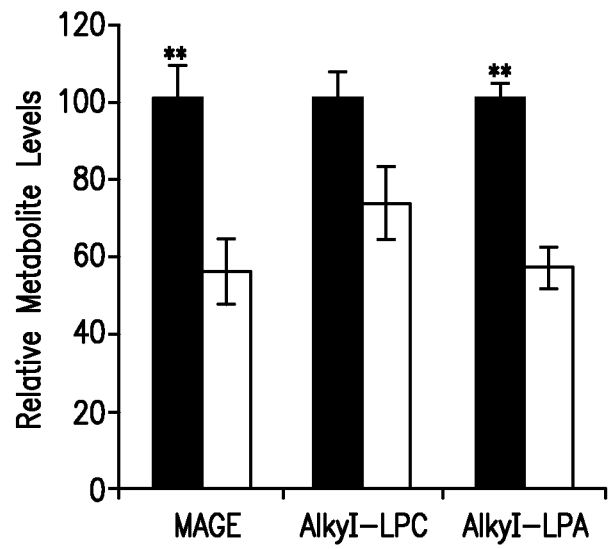
FIG. 10 shows that knockdown of the active protein by shRNA disrupts alkylglycerol lipid metabolism in breast cancer cells and impairs tumor growth in vivo. A) Reduction in the endogenous levels of MAGE, LPC, and LPA in KIAA1363 knock down cells. B) KIAA1363 knockdown cells show reduced tumor growth in vivo.
Figure 10B:
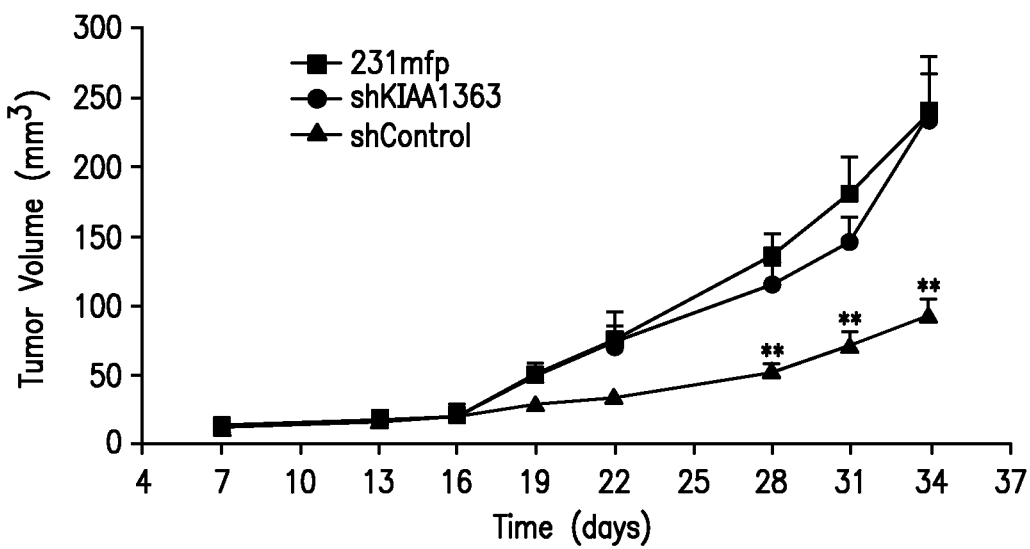

To determine whether a stable knockdown of the active protein impairs tumor growth in vivo, a SKOV-3 line can be utilized. A SKOV-3 line was generated in which the expression of the active protein was selectively and stably decreased by a short-hairpin RNA (shRNA)-mediate interference vector (shKIAA1363 cells). An additional control line (shControl) was also generated in which a distinct hydrolytic enzyme [dipeptidylpeptidase IV (DPPIV)] was knocked-down by a specific shRNA probe.

shKIAA1363 cells showed an approximately 70 to 75% reduction of this enzyme compared to control cells (shControl or parental SKOV-3 cells) (FIG. 8A), which correlated with a similar magnitude decrease in 2-acetyl MAGE hydrolase activity (FIG. 8B) and the levels of MAGE, alkyl-LPC, and alkyl-LPA lipids (FIG. 8C). The levels of other hydrolytic enzymes were not affected in shKIAA1363 cells, as judged by gel-based ABPP. On FIG. 8, p<0.01, and the results represent the average values t standard error for three independent experiments.

shKIAA1363 and control SKOV-3 cells were next compared for their tumor growth capacity by subcutaneous injection into immune-deficient mice. shKIAA363 SKOV-3 cells exhibited significantly reduced tumor growth rates compared to either shControl cells or the parental SKOV-3 line (FIG. 9A). shRNA-mediated knockdown of the active protein was also performed in the aggressive breast cancer line MDA-MB-231, resulting in lowered MAGE and lysophospholipid levels in these cells and impaired tumor growth in vivo (FIG. 10).

Figure 9B:
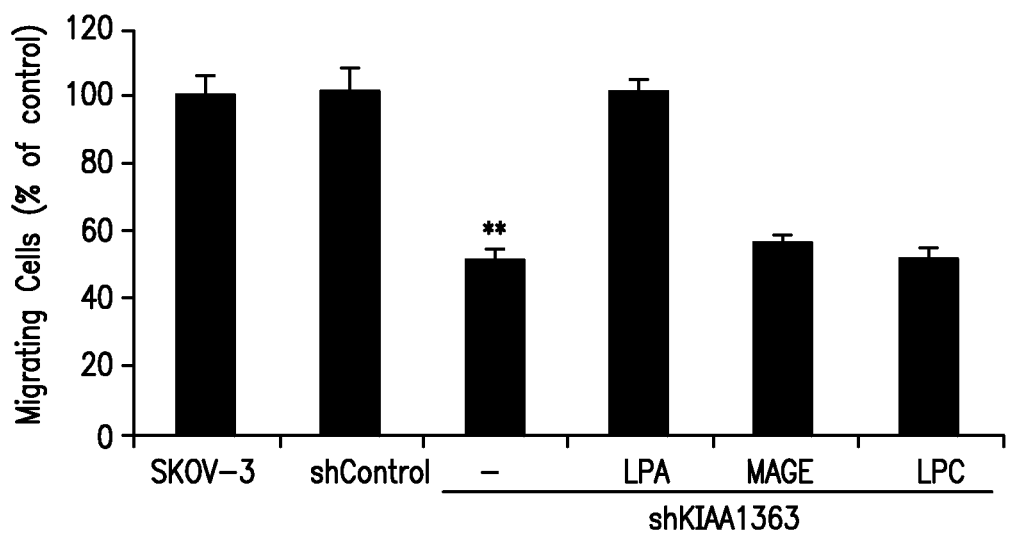
Figure 11:
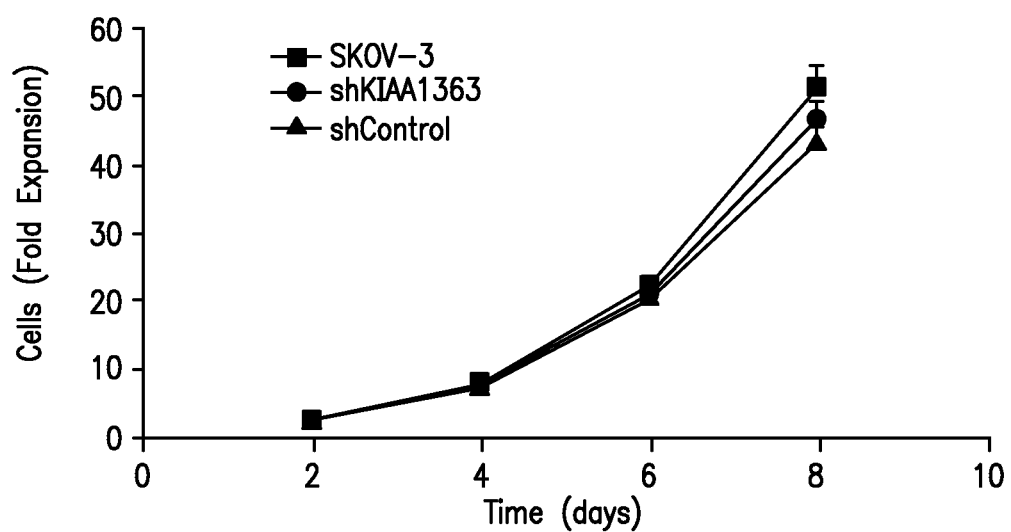
FIG. 11 shows that knockdown of the active protein by shRNA does not alter the proliferation rates of SKOV3 cells compared to control cells.

The decrease in tumorigenic potential of shKIAA1363 cells was not associated with a change in proliferation potential in vitro (FIG. 11). shKIAA1363 cells were, however, impaired in their in vitro migration capacity compared to control cells (FIG. 9B). To discern whether any of the lipids regulated by the active protein might contribute to cancer cell migration, the pharmacological effects of these compounds on shKIAA1363 cells were tested. Neither MAGE nor alkyl-LPC impacted cancer cell migration at concentrations up to 1 μM (FIG. 9B). In contrast, alkyl-LPA (10 nM) completely rescued the reduced migratory activity of shKIAA1363 cells.

Example 20

Substrate-Based Assay

Host cell lines expressing the SV-40 T antigen, such as human embryonic kidney cells (293T) or monkey kidney (COS-7) cells, were transiently transfected with a pFLAG-CMV6c (Sigma) construct containing KIAA1363. Note that other constructs may be used, such as pFLAG-CMV4. These result in N-terminal FLAG tagging of KIAA1363. Alternative N-terminal tags such as 6×his may also be used. Also, stable cell lines may also be established by antibiotic selection of the transfected cells.

At 48 h post-transfection, 293l or COS-7 cells transfected with KIAA1363 in pFLAG-CMV6c were harvested and the cells lysed in 50 mM tris buffer pH 7.4 by dounce homogenization and sonication. The lysate was subjected to ultracentrifugation at 100,000×g for 1 h at 4° C. The membrane fraction was washed by resuspending the pellet in 50 mM Tris buffer pH 7.4 by sonication and centrifuging again at 100,000×g for 1 h at 4° C.

The membrane pellet was resuspended in 50 mM tris buffer pH 7.4 by sonication. The protein content of the membrane fraction was determined and adjusted to 0.5 mg/ml in 50 mM tris buffer pH 7.4 containing 5 mM CHAPS detergent.

KIAA1363-transfected cell lines were used for substrate-based enzyme activity assays. Membrane proteomes were adjusted to 0.5 mg/ml in 50 mM tris pH 7.4 buffer containing 5 mM CHAPS detergent. Immediately prior to the assay, 5,5'-dithiobis-(2-nitrobenzoic acid) (DTNB, Sigma) was added at 0.5 mM to the membrane proteome to prepare the Assay Buffer. For analysis of inhibitors, 1 ul of a 50× inhibitor solution in DMSO was added to 48 ul of Assay Buffer and preincubated for 20 min at RT. The substrate 2-thioacetyl MAGE (Cayman Chemical) was prepared by evaporating off the original solvent under nitrogen and redissolving the residue in DMSO. 1 ul of 5 mM 2-thioacetyl MAGE stock is added to each assay well to begin the assay. Absorbance is determined at A405 nm.

Figure 13:
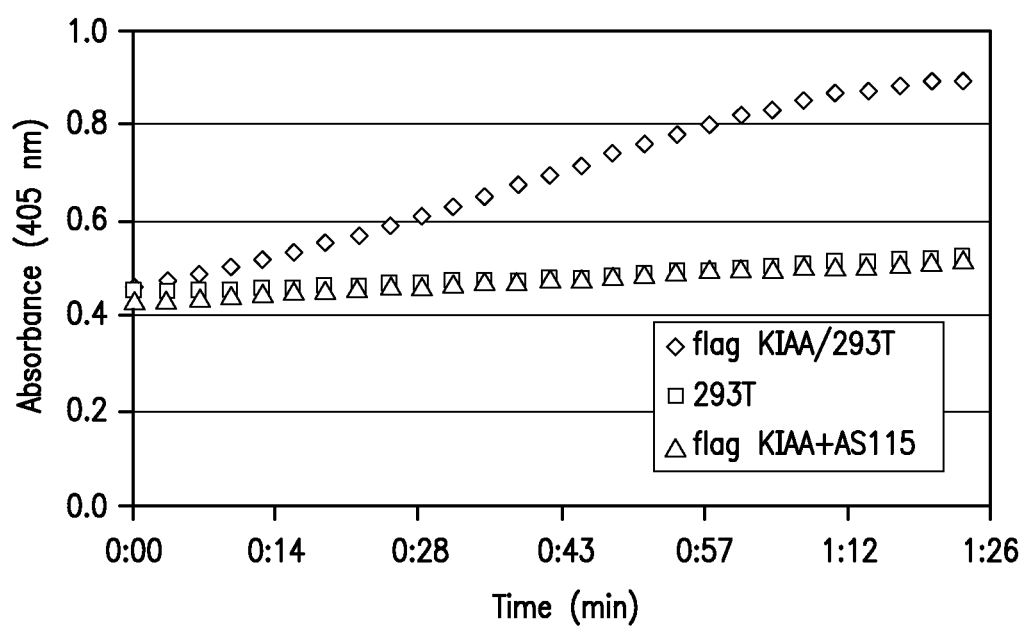
FIG. 13 illustrates 2-thioacetyl MAGE hydrolysis using Flag-KIAA1363/293T cell membrane proteome.
Figure 14:
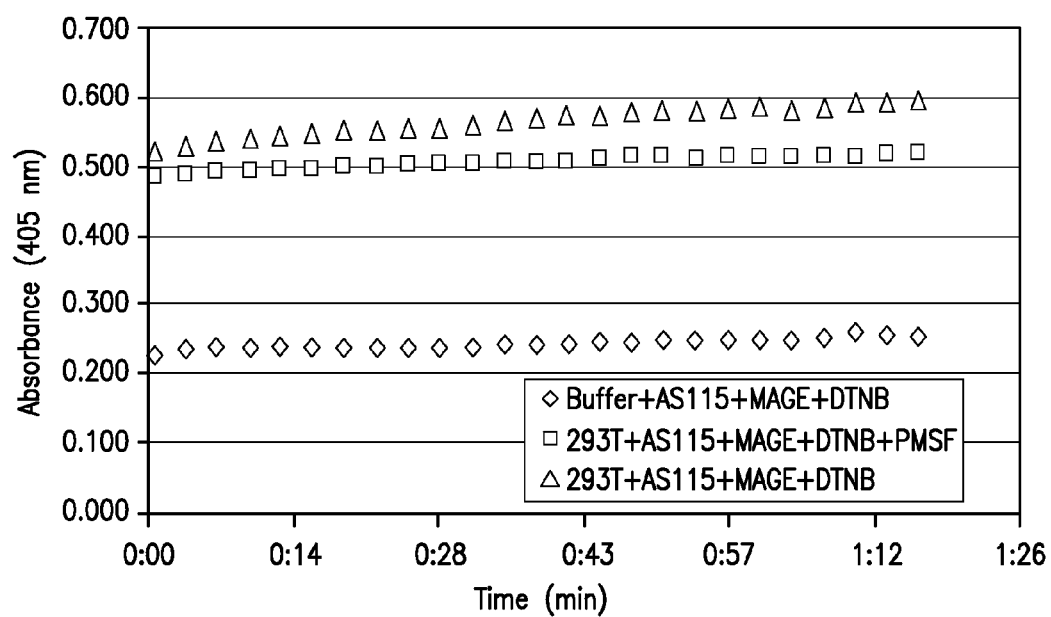
FIG. 14 illustrates background 2-thioacetyl MAGE hydrolyzing activity in membrane proteomes.
Figure 15:
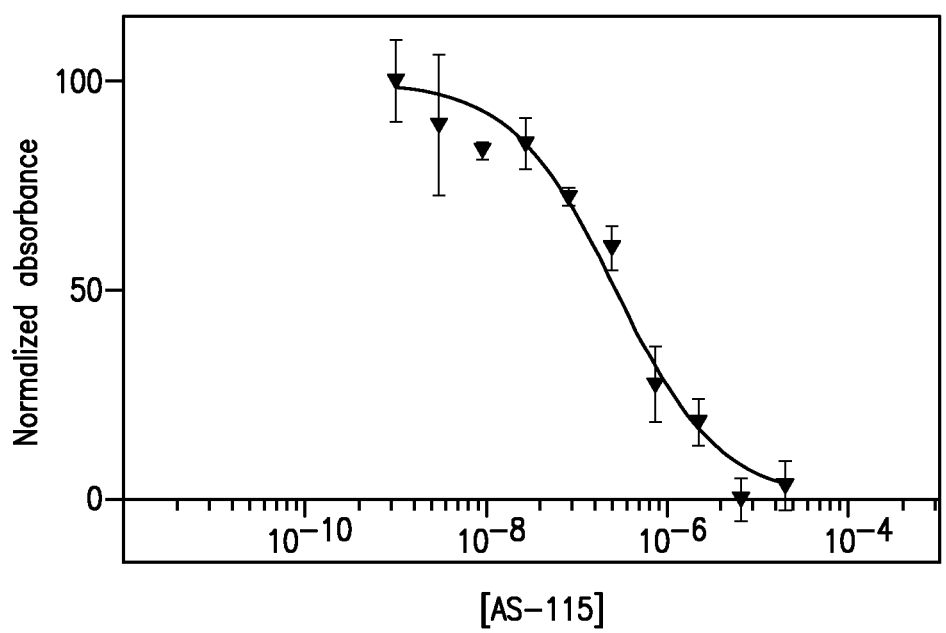
FIG. 15 illustrates the $IC_{50}$ of AS-115 using the 2-thioacetyl MAGE substrate-based assay with Flag-KIAA1363/293T cell membrane proteome. IC values ranged from 270 nM-620 nM.

Preincubation with 20 uM AS-115 fully inhibits the KIAA1363 activity to the level of nontransfected 293T cell membranes (FIG. 13). The background 2-thioacetyl MAGE hydrolyzing activity in membrane proteomes that is not inhibited by AS-115 is inhibited by the broad serine protease inhibitor PMSF (FIG. 14). The $IC_{50}$ of AS-115 was measured using the 2-thioacetyl MAGE substrate-based assay with Flag-KIAA1363/293T cell membrane proteome (FIG. 15).

Although the invention has been described with reference to the above examples, it will be understood that modifications and variations are encompassed within the spirit and scope of the invention. Accordingly, the invention is limited only by the following claims.

What is claimed is:

1. A method of identifying an inhibitor of neutral cholesterol ester hydrolase 1 (abbreviated as "KIAA1363") comprising:
   a) providing cells that express an amino acid sequence set forth in SEQ ID NO: 2;
   b) contacting the cells of step (a) with a first agent;
   c) determining the rate of 2-acetyl monoalkylglycerol (MAGE) hydrolysis, or a derivative thereof, in the presence of the agent;
   wherein when the rate of 2-acetyl MAGE hydrolysis decreases in the presence of the first agent, the decrease is indicative of an inhibitory effect of the first agent.

2. The method of claim 1, further comprising contacting the cells with a second agent, wherein the second agent modulates the expression of KIAA1363.

3. A method for identifying an inhibitor of KIAA1363 comprising
   a) isolating the membrane proteome from cells expressing KIAA1363;
   b) contacting the membrane proteome with a thiol-reactive fluorescent reagent and 2-thioacetyl monoalkylglycerol (2-thioacetyl MAGE), in the presence and absence of a test agent under conditions which allow hydrolysis of the 2-thioacetyl MAGE by KIAA1363; and
   c) determining the absorbance, wherein a decrease in the absorption in the presence of test compound as compared to the absorbance in the absence of test agent is indicative of an inhibitory effect of the test agent.

4. The method of claim 1, wherein the cells expressing KIAA1363 are host cells transfected with nucleic acid encoding KIAA1363.

5. The method of claim 4, wherein the nucleic acid encodes the amino acid sequence set forth in SEQ ID NO:2.

6. The method of claim 3, wherein the thiol-reactive fluorescent reagent is 5,5'-dithiobis-(2-nitrobenzoic acid) (DTNB).

* * * * *

SEQUENCE LISTING

<160> NUMBER OF SEQ ID NOS: 8

<210> SEQ ID NO 1
<211> LENGTH: 1323
<212> TYPE: DNA
<213> ORGANISM: Homo sapiens

<400> SEQUENCE: 1

| | |
|---|---:|
| atgagcagct gccgcgggca gaaagttgcc ggaggtctcc gggtggtatc gcccttttcct | 60 |
| ctttgccagc ccgctggcga gccgagccgg ggcaagatga ggtcgtcctg tgtcctgctc | 120 |
| accgccctgg tggcgctggc cgcctattac gtctacatcc cgctgcctgg ctccgtgtcc | 180 |
| gaccccctgga agctgatgct gctggacgcc actttccggg gtgcacagca agtgagtaac | 240 |
| ctgatccact acctgggact gagccatcac ctgctggcac tgaattttat cattgtttct | 300 |
| tttggcaaaa aaagcgcgtg gtcttctgcc caagtgaagg tgaccgacac agactttgat | 360 |
| ggtgtggaag tcagagtgtt tgaaggccct ccgaagcccg aagagccact gaaacgcagc | 420 |
| gtcgtttata tccacggagg aggctgggcc ttggcaagtg caaaaatcag gtattatgat | 480 |
| gagctgtgta cagcaatggc tgaggaattg aatgctgtca ttgtttccat gaatacagg | 540 |
| ctagttccaa aggtttattt tcctgagcaa attcatgatg ttgtacgggc acaaagtat | 600 |
| ttcctgaagc cagaagtctt acagaagtat atggttgatc caggcagaat ttgcatttct | 660 |
| ggtgacagtg ctggtggaaa tctggctgct gcccttggac aacagtttac tcaagatgcc | 720 |
| agcctaaaaa ataagctcaa actacaagct ttaatttatc cagttcttca agctttagat | 780 |
| tttaacacac catcttatca gcaaaatgtg aacaccccaa tcctgccccg ctatgtcatg | 840 |
| gtgaagtatt gggtggacta cttcaaaggc aactatgact ttgtgcaggc aatgatcgtt | 900 |
| aacaatcaca cttcacttga tgtggaagag gctgctgctg tcagggcccg tctaaactgg | 960 |
| acatccctct gcctgcatc cttcacaaag aactacaagc tgttgtaca gaccacaggc | 1020 |
| aatgccagga ttgtccagga gcttcctcag ttgctggatg cccgctccgc cccactcatt | 1080 |
| gcagaccagg cagtgctgca gctcctccca aagacctaca ttctgacgtg tgagcatgat | 1140 |
| gtcctcagag acgatggcat catgtatgcc aagcgtttgg agagtgccgg tgtggaggtg | 1200 |
| accctggatc actttgagga tggctttcac ggatgtatga ttttcactag ctggcccacc | 1260 |
| aacttctcag tgggaatccg gactaggaat agttacatca gtggctaga tcaaaacctg | 1320 |
| taa | 1323 |

<210> SEQ ID NO 2
<211> LENGTH: 440
<212> TYPE: PRT
<213> ORGANISM: Homo sapiens

<400> SEQUENCE: 2

Met Ser Ser Cys Arg Gly Gln Lys Val Ala Gly Gly Leu Arg Val Val
1               5                   10                  15

Ser Pro Phe Pro Leu Cys Gln Pro Ala Gly Glu Pro Ser Arg Gly Lys
            20                  25                  30

Met Arg Ser Ser Cys Val Leu Leu Thr Ala Leu Val Ala Leu Ala Ala
        35                  40                  45

Tyr Tyr Val Tyr Ile Pro Leu Pro Gly Ser Val Ser Asp Pro Trp Lys
    50                  55                  60

Leu Met Leu Leu Asp Ala Thr Phe Arg Gly Ala Gln Gln Val Ser Asn
65                  70                  75                  80

-continued

```
Leu Ile His Tyr Leu Gly Leu Ser His His Leu Leu Ala Leu Asn Phe
             85                  90                  95

Ile Ile Val Ser Phe Gly Lys Lys Ser Ala Trp Ser Ser Ala Gln Val
        100                 105                 110

Lys Val Thr Asp Thr Asp Phe Asp Gly Val Glu Val Arg Val Phe Glu
            115                 120                 125

Gly Pro Pro Lys Pro Glu Pro Leu Lys Arg Ser Val Val Tyr Ile
130             135                 140

His Gly Gly Gly Trp Ala Leu Ala Ser Ala Lys Ile Arg Tyr Tyr Asp
145                 150                 155                 160

Glu Leu Cys Thr Ala Met Ala Glu Glu Leu Asn Ala Val Ile Val Ser
                165                 170                 175

Ile Glu Tyr Arg Leu Val Pro Lys Val Tyr Phe Pro Glu Gln Ile His
            180                 185                 190

Asp Val Val Arg Ala Thr Lys Tyr Phe Leu Lys Pro Glu Val Leu Gln
            195                 200                 205

Lys Tyr Met Val Asp Pro Gly Arg Ile Cys Ile Ser Gly Asp Ser Ala
210             215                 220

Gly Gly Asn Leu Ala Ala Ala Leu Gly Gln Gln Phe Thr Gln Asp Ala
225                 230                 235                 240

Ser Leu Lys Asn Lys Leu Lys Leu Gln Ala Leu Ile Tyr Pro Val Leu
                245                 250                 255

Gln Ala Leu Asp Phe Asn Thr Pro Ser Tyr Gln Gln Asn Val Asn Thr
            260                 265                 270

Pro Ile Leu Pro Arg Tyr Val Met Val Lys Tyr Trp Val Asp Tyr Phe
            275                 280                 285

Lys Gly Asn Tyr Asp Phe Val Gln Ala Met Ile Val Asn Asn His Thr
290                 295                 300

Ser Leu Asp Val Glu Glu Ala Ala Val Arg Ala Arg Leu Asn Trp
305                 310                 315                 320

Thr Ser Leu Leu Pro Ala Ser Phe Thr Lys Asn Tyr Lys Pro Val Val
                325                 330                 335

Gln Thr Thr Gly Asn Ala Arg Ile Val Gln Glu Leu Pro Gln Leu Leu
            340                 345                 350

Asp Ala Arg Ser Ala Pro Leu Ile Ala Asp Gln Ala Val Leu Gln Leu
            355                 360                 365

Leu Pro Lys Thr Tyr Ile Leu Thr Cys Glu His Asp Val Leu Arg Asp
            370                 375                 380

Asp Gly Ile Met Tyr Ala Lys Arg Leu Glu Ser Ala Gly Val Glu Val
385                 390                 395                 400

Thr Leu Asp His Phe Glu Asp Gly Phe His Gly Cys Met Ile Phe Thr
            405                 410                 415

Ser Trp Pro Thr Asn Phe Ser Val Gly Ile Arg Thr Arg Asn Ser Tyr
            420                 425                 430

Ile Lys Trp Leu Asp Gln Asn Leu
            435                 440

<210> SEQ ID NO 3
<211> LENGTH: 30
<212> TYPE: DNA
<213> ORGANISM: Artificial sequence
<220> FEATURE:
<223> OTHER INFORMATION: Primer

<400> SEQUENCE: 3
```

```
cgcggatcca tgaggtcgtc ctgtgtcctg                                           30
```

<210> SEQ ID NO 4
<211> LENGTH: 28
<212> TYPE: DNA
<213> ORGANISM: Artificial sequence
<220> FEATURE:
<223> OTHER INFORMATION: Primer

<400> SEQUENCE: 4

```
cggaattctt acaggttttg atctagcc                                             28
```

<210> SEQ ID NO 5
<211> LENGTH: 19
<212> TYPE: DNA
<213> ORGANISM: Artificial sequence
<220> FEATURE:
<223> OTHER INFORMATION: Oligonucleotide

<400> SEQUENCE: 5

```
tgtgaacacc ccaatcctg                                                       19
```

<210> SEQ ID NO 6
<211> LENGTH: 19
<212> TYPE: DNA
<213> ORGANISM: Artificial sequence
<220> FEATURE:
<223> OTHER INFORMATION: Oligonucleotide

<400> SEQUENCE: 6

```
gattcttctg ggactgctg                                                       19
```

<210> SEQ ID NO 7
<211> LENGTH: 1227
<212> TYPE: DNA
<213> ORGANISM: Mouse

<400> SEQUENCE: 7

```
atgaggtcgt catgcgtcct actggccgct ctgctggctc tggctgccta ctacgtgtac          60
atcccactgc ccagcgcggt gtccgacccc tggaaactga tgctgctgga cgccactttc         120
cgcggcgcgc agcaagtgag taacctgata cattccctgg gactgaacca ccatctgatc         180
gcgctgaatt tcatcatcac ctcttttggc aagcaaagcg caaggtcttc tccgaaagtg         240
aaggtgacag acaccgactt cgatggggta gaagtccgag tatttgaagg ttctccgaaa         300
ccagaagagc cgctgcgacg cagcgtcatc tatatccacg gaggaggctg ggccctggct         360
agtgcaaaga tcagctacta tgaccagctg tgcacaacaa tggctgagga gctgaacgcc         420
gtcatcgttt ctattgaata caggctagtc ccacaggtct attttccgga gcaaatccat         480
gatgtcatcc gtgccactaa atatttcctg cagccagaag tcttagacaa gtacaaggtc         540
gaccctggaa gagtcggtat ttctggagac agtgctggtg ggaatctggc cgcggccctg         600
ggacaacagt ttacctacgt tgccagcctg aagaataagc tcaaactgca ggctttggtc         660
tacccagtcc tgcaggcttt ggacttcaac acaccctctt accagcaaag catgaacact         720
ccgatcctgc cgcgtcatgt catggttagg tactggttag actacttcaa gggcaactac         780
gactttgtag aggccatgat tgtgaacaat cacacttcac ttgatgtaga aagggctgca         840
gccctcaggg cccgtctcga ctggacatcc ctgttgccct cgtccatcaa aaagaactac         900
aagcctatca tgcagaccac agggaacgcc aggatcgtcc aggagatccc tcaactgctg         960
gacgctgctg cttctccgct catcgcagag caggaagtgc tagaggccct cccgaagacc        1020
```

```
tacatcctta cctgcgagca cgacgtcctg cgggacgatg ggatcatgta cgccaagcgc    1080
ttggagagtg cgggtgtgaa cgtgaccttg gaccactttg aggacggctt ccatggttgt    1140 atgatttta caagctggcc gaccaacttc tccgtgggaa tccggactag gaatagttac    1200
atcaaatggc tggatcaaaa cctgtga                                        1227
```

<210> SEQ ID NO 8
<211> LENGTH: 408
<212> TYPE: PRT
<213> ORGANISM: Mouse

<400> SEQUENCE: 8

```
Met Arg Ser Ser Cys Val Leu Leu Ala Ala Leu Leu Ala Leu Ala Ala
1               5                   10                  15

Tyr Tyr Val Tyr Ile Pro Leu Pro Ser Ala Val Ser Asp Pro Trp Lys
            20                  25                  30

Leu Met Leu Leu Asp Ala Thr Phe Arg Gly Ala Gln Gln Val Ser Asn
        35                  40                  45

Leu Ile His Ser Leu Gly Leu Asn His His Leu Ile Ala Leu Asn Phe
    50                  55                  60

Ile Ile Thr Ser Phe Gly Lys Gln Ser Ala Arg Ser Ser Pro Lys Val
65                  70                  75                  80

Lys Val Thr Asp Thr Asp Phe Asp Gly Val Glu Val Arg Val Phe Glu
                85                  90                  95

Gly Ser Pro Lys Pro Glu Glu Pro Leu Arg Arg Ser Val Ile Tyr Ile
            100                 105                 110

His Gly Gly Gly Trp Ala Leu Ala Ser Ala Lys Ile Ser Tyr Tyr Asp
        115                 120                 125

Gln Leu Cys Thr Thr Met Ala Glu Glu Leu Asn Ala Val Ile Val Ser
    130                 135                 140

Ile Glu Tyr Arg Leu Val Pro Gln Val Tyr Phe Pro Glu Gln Ile His
145                 150                 155                 160

Asp Val Ile Arg Ala Thr Lys Tyr Phe Leu Gln Pro Glu Val Leu Asp
                165                 170                 175

Lys Tyr Lys Val Asp Pro Gly Arg Val Gly Ile Ser Gly Asp Ser Ala
            180                 185                 190

Gly Gly Asn Leu Ala Ala Ala Leu Gly Gln Gln Phe Thr Tyr Val Ala
        195                 200                 205

Ser Leu Lys Asn Lys Leu Lys Leu Gln Ala Leu Val Tyr Pro Val Leu
    210                 215                 220

Gln Ala Leu Asp Phe Asn Thr Pro Ser Tyr Gln Gln Ser Met Asn Thr
225                 230                 235                 240

Pro Ile Leu Pro Arg His Val Met Val Arg Tyr Trp Leu Asp Tyr Phe
                245                 250                 255

Lys Gly Asn Tyr Asp Phe Val Glu Ala Met Ile Val Asn Asn His Thr
            260                 265                 270

Ser Leu Asp Val Glu Arg Ala Ala Ala Leu Arg Ala Arg Leu Asp Trp
        275                 280                 285

Thr Ser Leu Leu Pro Ser Ile Lys Lys Asn Tyr Lys Pro Ile Met
    290                 295                 300

Gln Thr Thr Gly Asn Ala Arg Ile Val Gln Glu Ile Pro Gln Leu Leu
305                 310                 315                 320

Asp Ala Ala Ala Ser Pro Leu Ile Ala Glu Gln Glu Val Leu Glu Ala
                325                 330                 335
```

```
Leu Pro Lys Thr Tyr Ile Leu Thr Cys Glu His Asp Val Leu Arg Asp
            340             345             350

Asp Gly Ile Met Tyr Ala Lys Arg Leu Glu Ser Ala Gly Val Asn Val
            355             360             365

Thr Leu Asp His Phe Glu Asp Gly Phe His Gly Cys Met Ile Phe Thr
        370             375             380

Ser Trp Pro Thr Asn Phe Ser Val Gly Ile Arg Thr Arg Asn Ser Tyr
385             390             395             400

Ile Lys Trp Leu Asp Gln Asn Leu
                405
```